(12) United States Patent
Strother et al.

(10) Patent No.: US 7,878,981 B2
(45) Date of Patent: Feb. 1, 2011

(54) SYSTEMS AND METHODS FOR INTRA-OPERATIVE STIMULATION

(75) Inventors: Robert B. Strother, Willoughby Hills, OH (US); Geoffrey B. Thrope, Shaker Heights, OH (US); Joseph J. Mrva, Euclid, OH (US); Steven M. Galecki, Concord, OH (US); Danny R. Pack, Avon Lake, OH (US); Christopher A. Thierfelder, Minneapolis, MN (US); James Coburn, Cleveland Heights, OH (US)

(73) Assignee: Checkpoint Surgical, LLC, Cleveland, OH (US)

( * ) Notice: Subject to any disclaimer, the term of this patent is extended or adjusted under 35 U.S.C. 154(b) by 0 days.

(21) Appl. No.: 11/651,165

(22) Filed: Jan. 9, 2007

(65) Prior Publication Data
US 2007/0191915 A1    Aug. 16, 2007

Related U.S. Application Data

(63) Continuation-in-part of application No. 11/099,848, filed on Apr. 6, 2005.

(60) Provisional application No. 60/657,277, filed on Mar. 1, 2005.

(51) Int. Cl.
*A61B 5/05* (2006.01)
*A61N 1/00* (2006.01)

(52) U.S. Cl. .................. 600/554; 607/115; 607/145; 607/146

(58) Field of Classification Search .................. 600/554; 607/2–76, 115–156
See application file for complete search history.

(56) References Cited

U.S. PATENT DOCUMENTS

| | | | |
|---|---|---|---|
| 4,515,168 A * | 5/1985 | Chester et al. | ............... 600/554 |
| 4,545,374 A | 10/1985 | Jacobson | |
| 4,616,660 A | 10/1986 | Johns | |
| 4,777,960 A | 10/1988 | Berger et al. | |
| 4,962,766 A * | 10/1990 | Herzon | ........................ 600/554 |
| 5,012,816 A | 5/1991 | Lederer | |

(Continued)

FOREIGN PATENT DOCUMENTS

WO        WO03/005887 A2       1/2003

OTHER PUBLICATIONS

IP Classification Guide; http://web.archive.org/web/20060526074548/http://www.capax.se/solutions/IP_classification.htm (IPCG) May 26, 2006.

*Primary Examiner*—Max Hindenburg
*Assistant Examiner*—John Pani
(74) *Attorney, Agent, or Firm*—Ryan Kromholz & Manion, S.C.

(57) ABSTRACT

Improved assemblies, systems, and methods provide safeguarding against tissue injury during surgical procedures and/or identify nerve damage occurring prior to surgery and/or verify range of motion or attributes of muscle contraction during reconstructive surgery. A stimulation control device may incorporate a range of low and high intensity stimulation to provide a stimulation and evaluation of both nerves and muscles. A stimulation control device is removably coupled to a surgical device or is imbedded within the medical device to provide a stimulation and treatment medical device. A disposable hand held stimulation system includes an operative element extending from the housing, the housing includes an operative element adjustment portion and a visual indication to provide feedback or status to the user.

12 Claims, 13 Drawing Sheets

U.S. PATENT DOCUMENTS

| | | | |
|---|---|---|---|
| 5,046,506 A | 9/1991 | Singer | |
| 5,086,788 A | 2/1992 | Casteel et al. | |
| 5,284,153 A | 2/1994 | Raymond et al. | |
| 5,284,154 A | 2/1994 | Raymond et al. | |
| 5,540,235 A | 7/1996 | Wilson | |
| 5,775,331 A * | 7/1998 | Raymond et al. | 600/554 |
| 5,779,642 A | 7/1998 | Nightengale | |
| 5,879,289 A * | 3/1999 | Yarush et al. | 600/179 |
| 5,885,219 A | 3/1999 | Nightengale | |
| 5,928,158 A * | 7/1999 | Aristides | 600/547 |
| 6,091,995 A | 7/2000 | Ingle et al. | |
| 6,139,545 A | 10/2000 | Utley et al. | |
| 6,292,701 B1 | 9/2001 | Prass et al. | |
| 6,304,785 B1 | 10/2001 | McCreery et al. | |
| 6,306,100 B1 * | 10/2001 | Prass | 600/554 |
| 6,312,392 B1 | 11/2001 | Herzon | |
| 6,325,764 B1 * | 12/2001 | Griffith et al. | 600/554 |
| 6,334,068 B1 | 12/2001 | Hacker | |
| 6,473,511 B1 * | 10/2002 | Aceti et al. | 381/322 |
| 6,494,882 B1 | 12/2002 | Lebouitz et al. | |
| 6,542,260 B1 | 4/2003 | Gann et al. | |
| 6,609,018 B2 | 8/2003 | Cory et al. | |
| 6,612,983 B1 | 9/2003 | Marchal | |
| 6,618,626 B2 | 9/2003 | West, Jr. et al. | |
| 6,654,634 B1 | 11/2003 | Prass | |
| 6,829,508 B2 | 12/2004 | Schulman et al. | |
| 6,972,199 B2 | 12/2005 | Lebouitz et al. | |
| 6,975,708 B1 | 12/2005 | Scherer | |
| 7,010,352 B2 | 3/2006 | Hogan | |
| 7,207,949 B2 | 4/2007 | Miles et al. | |
| 7,282,033 B2 | 10/2007 | Urmey | |
| 7,470,236 B1 | 12/2008 | Kelleher et al. | |
| 7,522,953 B2 | 4/2009 | Kaula et al. | |
| 7,555,347 B2 | 6/2009 | Loeb | |
| 2004/0078056 A1 | 4/2004 | Zangen et al. | |
| 2004/0215184 A1 | 10/2004 | Eggers et al. | |
| 2005/0256541 A1 | 11/2005 | Stypulkowski | |
| 2006/0011022 A1 * | 1/2006 | Fairburn et al. | 81/300 |
| 2006/0025702 A1 * | 2/2006 | Sterrantino et al. | 600/554 |
| 2006/0200219 A1 | 9/2006 | Thrope et al. | |

\* cited by examiner

SYSTEMS AND METHODS FOR INTRA-OPERATIVE STIMULATION

RELATED APPLICATIONS

This application is a continuation-in-part of copending U.S. patent application Ser. No. 11/099,848, filed Apr. 6, 2005, and entitled "Systems and Methods for Intra-Operative Stimulation," which claims the benefit of U.S. Provisional Patent Application Ser. No. 60/657,277, filed Mar. 1, 2005, and entitled "Systems and Methods for Intra-Operative Stimulation" which is incorporated herein by reference.

FIELD OF THE INVENTION

The invention relates generally to tissue identification and integrity testing, and more particularly to systems and methods for safeguarding against nerve and muscle injury during surgical procedures, location and stimulation of nerves and muscles, identification and assessment of nerve and muscle integrity following traumatic injuries, and verification of range of motion and attributes of muscle contraction during reconstructive surgery.

BACKGROUND OF THE INVENTION

Even with today's sophisticated medical devices, surgical procedures are not risk-free. Each patient's anatomy differs, requiring the surgeon to be ever vigilant to these differences so that the intended result is accomplished. The positioning of nerves and other tissues within a human or animal's body is one example of how internal anatomy differs from patient to patient. While these differences may be slight, if the surgeon fails to properly identify one or several nerves, the nerves may be bruised, stretched, or even severed during an operation. The negative effects of nerve damage can range from lack of feeling on that part of the body to loss of muscle control.

Traumatic injuries often require surgical repair. Determining the extent of muscle and nerve injury is not always possible using visual inspection. Use of an intra-operative stimulator enables accurate evaluation of the neuromuscular system in that area. This evaluation provides valuable knowledge to guide repair/reconstructive surgery following traumatic injury, and when performing a wide range of surgeries.

SUMMARY OF THE INVENTION

The invention provides devices, systems, and methods for intra-operative stimulation. The intra-operative stimulation enables accurate evaluation of the neuromuscular system to guide repair or reconstructive surgery.

One aspect of the invention provides devices, systems, and methods comprising a tissue stimulation system having a housing having a proximal end and a distal end, an operative element having an electrically conductive surface sized and configured for electrical stimulation of a targeted tissue region, and the operative element extends from the proximal end of the housing. The housing proximal end comprises an operative element adjustment portion to allow movement of the operative element, with the electrical stimulation being in the form of a stimulation signal having an amplitude and a duration for providing a first indication. A stimulation control device is electrically coupled to the operative element, the stimulation control device comprising a power source and stimulation signal generating circuitry. The tissue stimulation system may conform to the IPX1 water ingress standard.

In one aspect of the invention, the stimulation control device is positioned within the housing. The housing comprises a gripping base portion and the operative element adjustment portion. The operative element adjustment portion comprises a flexible nose cone.

The first indication comprises a visual indication located on the housing, and the housing may be tubular. The visual indication may also include a reflective element. The visual indication may comprise an illuminating circumferential ring indicator, the illuminating circumferential ring indicator being visible around the circumference of the tubular housing.

Yet another aspect of the invention provides devices, systems, and methods comprising a tissue stimulation system comprising a housing, such as a tubular shaped housing, having a proximal end and a distal end, an operative element having an electrically conductive surface sized and configured for electrical stimulation of a targeted tissue region, the operative element extending from the proximal end of the housing, and wherein the electrical stimulation is in the form of a signal having an amplitude and a duration for providing a first indication to the user of close proximity of the operative element to the targeted tissue region, and a stimulation control device electrically coupled to the operative element, the stimulation control device comprising stimulation signal generating circuitry. The housing may include a first control device for turning the stimulation signal to the operative element on and off and for providing adjustment of the stimulation signal amplitude, the first control device being electrically coupled to the stimulation control device. The housing may also include a second control device for providing adjustment of the stimulation signal duration, the second control device being electrically coupled to the stimulation control device.

Additional aspects of the invention provide a tissue stimulation system that may be sterilized using ethylene oxide, for example, and prepackaged for single use. The stimulation signal of the tissue stimulation system includes an amplitude that may range between about zero milliamps and about 20 milliamps, allowing for accurate selective stimulation of both muscles and nerves, and also identification of nerves and muscles, muscle attachments, or to contract muscles to assess the quality of surgical interventions. The tissue stimulation signal duration may include a range between about zero microseconds and about 200 microseconds, for example. The first indication provided by the tissue stimulation system may include, for example, audio and visual indications. The tissue stimulation system may further include a second indication means to provide confirmation of power on to the device and delivery of a stimulation signal to the electrically conductive surface. The first and second indication means may be combined into a single indication means. The operative element of the tissue stimulation system may comprise a probe, for example, where the electrically conductive surface of the probe comprises between about 1 millimeter and about 10 millimeters of the proximal end of the probe, and the probe comprises a diameter between about 0.5 millimeters and about 1.5 millimeters. The tissue stimulation system may also further include a return electrode electrically coupled to the stimulation control device.

Additional aspects of the invention provide a tissue stimulation system, such as a medical device comprising a housing having a proximal end and a distal end, the housing sized and configured to be held by a user in either the left or right hand, a probe having an electrically conductive surface sized and configured for electrical stimulation of a targeted tissue region, the probe extending from the proximal end of the housing. The housing proximal end comprises a probe adjustment portion to allow movement of the probe. The electrical stimulation is in the form of a signal having an amplitude and a duration for providing a physical motor response, a stimulation control device electrically coupled to the probe and sized and configured to be positioned within the housing, the stimulation control device comprising stimulation signal generating circuitry. The housing may include a first control device for turning the stimulation signal to the probe on and off and for providing adjustment of the stimulation signal amplitude, the first control device being electrically coupled to the stimulation control device. The housing may also include a second control device for providing adjustment of the stimulation signal duration, the second control device being electrically coupled to the stimulation control device.

According to another aspect of the invention, a stimulation control device electrically coupled to at least one surgical tool, which can comprise, e.g., a cutting, grasping, drilling, screwing, and/or viewing tool. The application of stimulation voltage or current to the device allows the clinician to observe muscle contraction or changes in the nervous system response when the surgical tool is in close proximity to viable nerve or muscle tissue. The surgical tool thus becomes a neural/muscular stimulating electrode. In use, different different medical procedures, can make use of a singe, stimulation control device, to which a selected surgical tool can be temporarily coupled for use.

According to yet another aspect of the invention, the stimulation control device may be embedded within the surgical tool to provide a medical device capable of providing stimulation, as described above.

Another aspect of the invention provides devices, systems, and methods comprising a stimulation monitor or probe and at least one electrode. In one embodiment, a hand held stimulation probe or monitor includes the stimulation control device and at least one stimulation electrode within a unified housing to provide an ergonomic stimulation device. The hand held stimulation probe can be a sterile, single use instrument intended for use during surgical procedures to identify nerves and muscles, muscle attachments, or to contract muscles to assess the quality of surgical interventions or the need for surgical interventions, or to evaluate the function of nerves already identified through visual or audible means, or by other nervous system monitoring instruments.

Yet another aspect of the invention provides devices, systems, and methods, including a method of testing a tissue region of a patient that includes providing a tissue stimulation system having an operative element extending from a proximal end of a housing, the housing proximal end comprising an operative element adjustment portion to allow movement of the operative element, moving a first control device to an activation position causing a stimulation signal to be generated by the stimulation system and transmitted to the operative element, engaging the patient with the operative element at a targeted tissue region, and observing the targeted tissue region for a first indication.

The method may further include engaging the patient with a second electrode which is electrically coupled to the stimulation system, the second electrode allowing the stimulation signal to flow from the operative element, through the patient's body to the second electrode, and back to the stimulation system.

Another aspect of the invention provides devices, systems, and methods comprising a hand held tissue stimulation apparatus including a tubular shaped housing comprising a gripping base portion and an operative element adjustment portion, the gripping base portion comprising a first housing element and a second housing element, a stimulation control device positioned within the gripping base portion, a battery positioned within the gripping base portion and coupled to the stimulation control device to provide power to the stimulation control device, a visual indication coupled to a proximal end of the gripping base portion, the visual indication comprising an illuminating circumferential ring indicator, the illuminating circumferential ring indicator being visible around the circumference of the tubular housing, and an operative element having an electrically conductive surface sized and configured for electrical stimulation of a targeted tissue region, the operative element being coupled to the stimulation control device and extending from the proximal end of the operative element adjustment portion.

The operative element adjustment portion comprises a flexible nose cone sized and configured to allow movement of the operative element, and the visual indication further includes a reflector element. A return electrode electrically may be coupled to the stimulation control device.

According to yet another aspect of the invention, a kit of devices provides tissue stimulation to a targeted tissue region. The kit may include a hand held stimulation probe including a housing sized and configured to be held with either a left or right hand, the stimulation probe being sterilized and disposable, and including an operative element extending from a proximal end of the housing, the housing proximal end comprising an operative element adjustment portion to allow movement of the operative element, a lead including a return electrode coupled to the stimulation probe, and instructions for use describing the unpacking and tissue contact procedure for the stimulation probe.

Additional aspects of the invention provide a stimulation control device electrically coupled to a tissue cutting instrument, or a stimulation control device electrically coupled to a drilling instrument, or a stimulation control device electrically coupled to a pilot auger for hard surface rotary probing prior to pilot hole drilling, or a stimulation control device electrically coupled to a fixation device, which is commonly used in spinal stabilization procedures and internal bone fixation procedures.

Features and advantages of the inventions are set forth in the following Description and Drawings, as well as the appended description of technical features.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF PREFERRED EMBODIMENTS

This Specification discloses various systems and methods for safeguarding against nerve, muscle, and tendon injury during surgical procedures or confirming the identity and/or location of nerves, muscles, and tendons and evaluating their function or the function of muscles enervated by those nerves. The systems and methods are particularly well suited for assisting surgeons in identification of nerves and muscles in order to assure nerve and muscle integrity during medical procedures using medical devices such as stimulation monitors, cutting, drilling, and screwing devices, pilot augers, and fixation devices. For this reason, the systems and methods will be described in the context of these medical devices.

The systems and methods desirably allow the application of a stimulation signal at sufficiently high levels for the purposes of locating, stimulating, and evaluating nerve or muscle, or both nerve and muscle integrity innumerous medical procedures, including, but not limited to, evaluating proximity to a targeted tissue region, evaluating proximity to a nerve or to identify nerve tissue, evaluating if a nerve is intact (i.e., following a traumatic injury) to determine if a repair may be needed, evaluating muscle contraction to determine whether or not the muscle is innervated and/or whether the muscle is intact and/or whether the muscle is severed, and evaluating muscle and tendon length and function following a repair or tendon transfer prior to completing a surgical procedure.

Still, it should be appreciated that the disclosed systems and methods are applicable for use in a wide variety of medical procedures with a wide variety of medical devices. By way of non-limiting example, the various aspects of the invention have application in procedures requiring grasping medical devices and internal viewing devices as well.

I. Overview of the System

Figure 1:
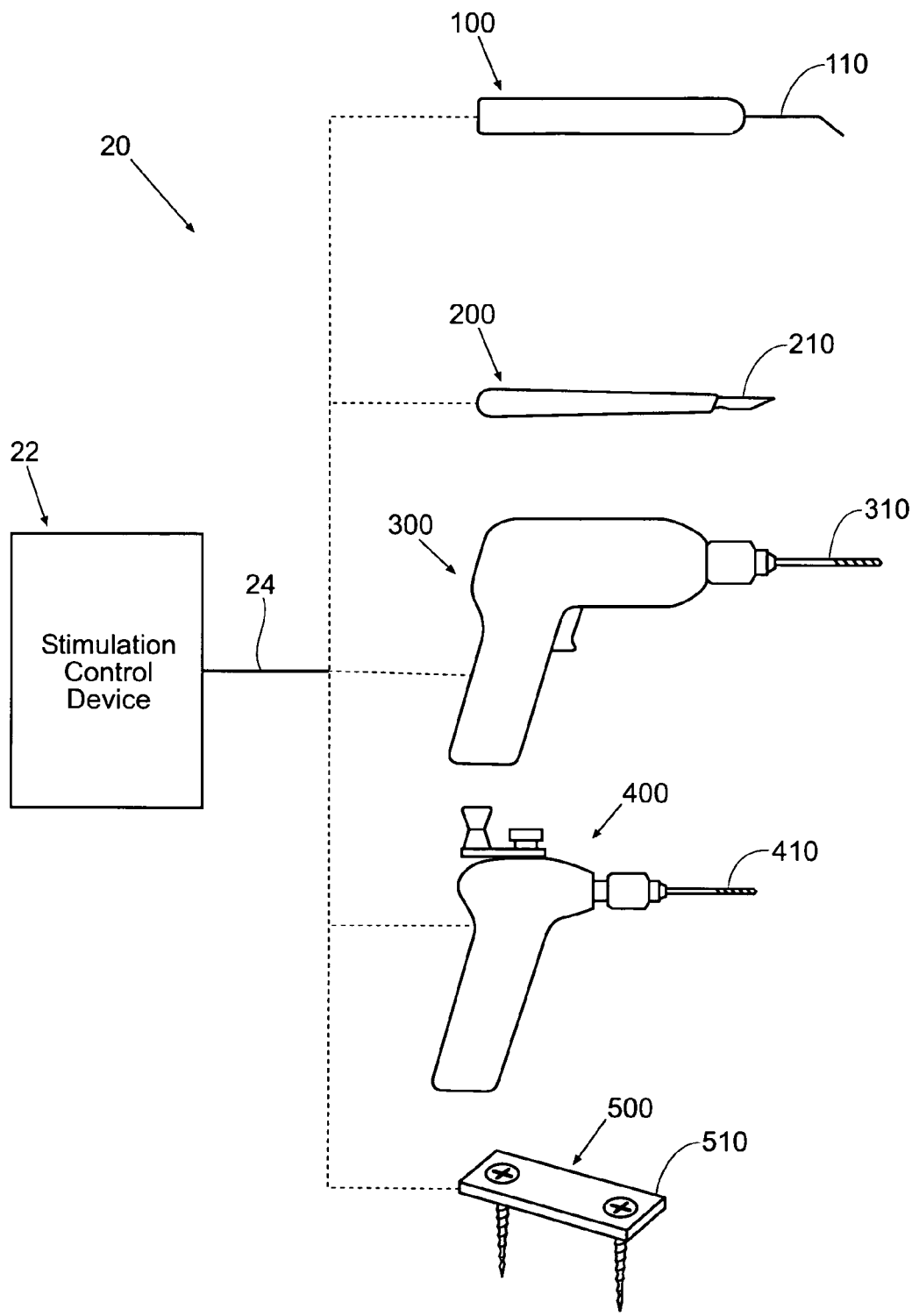
FIG. 1 is a diagrammatic view of a system usable in association with a family of different monitoring and treatment devices for use in different medical procedures.

FIG. 1 shows an illustrative system 20 for locating and identifying tissue and safeguarding against tissue and/or bone injury during surgical procedures. In the illustrated embodiment, the system 20 is configured for locating, monitoring, and stimulating tissue and other structures throughout the body. The system 20 includes a stimulation control device 22 operating individually or in conjunction with one or more of a family of stimulating medical devices including, for example, a stimulation monitor or probe 100, a cutting device 200, a drilling or screwing device 300, a pilot auger 400, and a fixation device 500.

Figure 2:
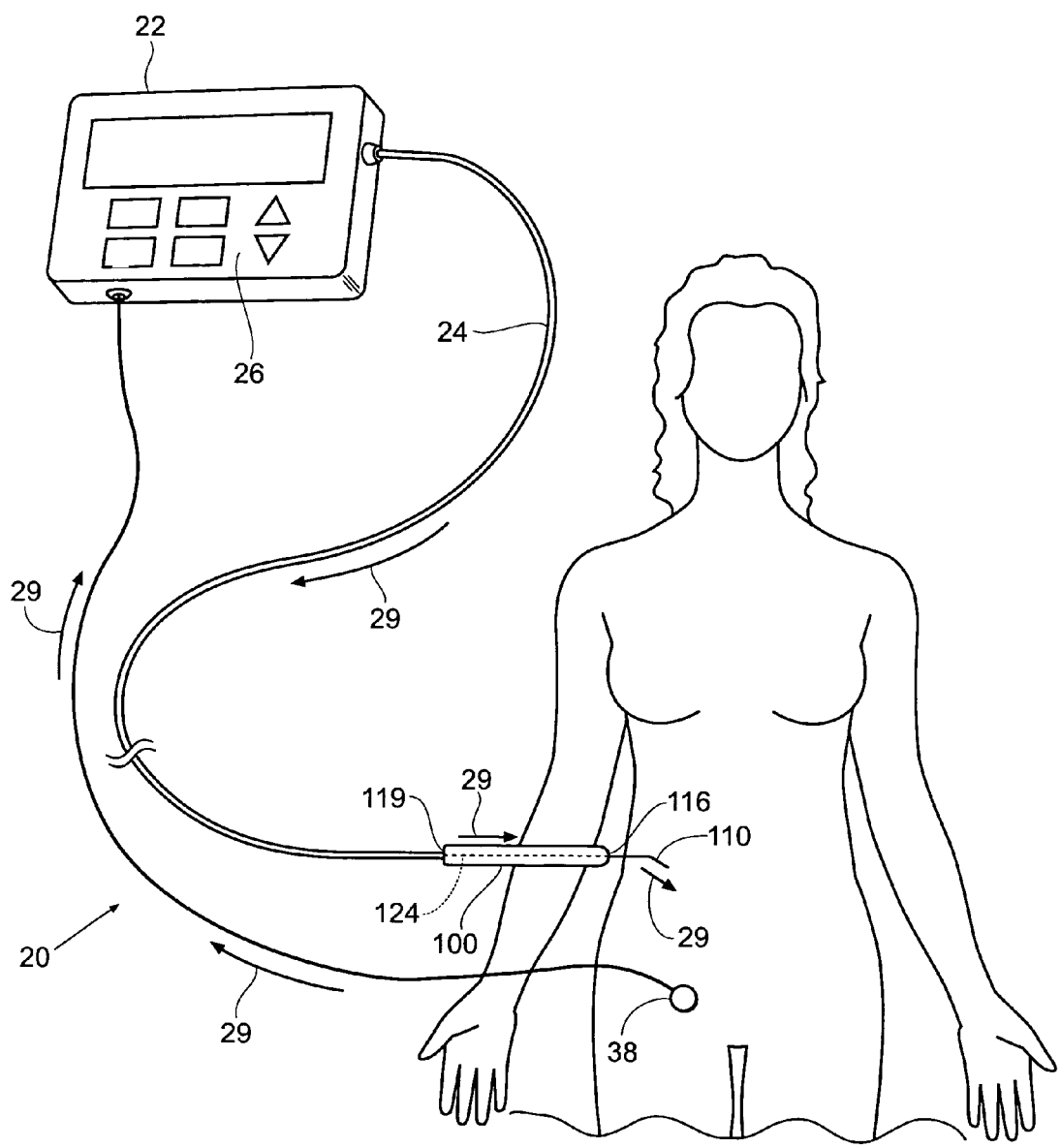
FIG. 2 is a perspective view showing an exemplary embodiment of the system shown in FIG. 1, the stimulation control device being removably coupled to a stimulation probe, and showing the stimulation signal path through the system.

In an exemplary embodiment, and as can be seen in FIG. 2, the stimulation control device 22 functions in the system 20 to generate an electrical stimulation signal 29. The stimulation signal 29 flows from the stimulation control device 22 through a lead 24 to a medical device (e.g., stimulation probe 100). The stimulation signal 29 then flows through a predefined insulated path 124 within the stimulation probe 100 and to an operative element, such as an electrically conductive surface, i.e., a coupled electrode 110. The electrode 110 is to be positioned on or near a region of a patient to be stimulated. In monopolar operation, a return electrode (or indifferent electrode) 38 provides an electrical path from the body back to the control device 22. The stimulation control device 22 may operate in a monopolar or bipolar configuration, as will be described in greater detail later.

The stimulation signal 29 is adapted to provide an indication or status of the device. The indication may include a physical motor response (e.g., twitching), and/or one or more visual or audio signals from the stimulation control device 22, which indicate to the surgeon the status of the device, and/or close proximity of the electrode 110 to a nerve, or a muscle, or a nerve and a muscle. The stimulation control device may also indicate to the surgeon that the stimulation control device is operating properly and delivering a stimulus current.

II. Medical Devices

The configuration of the stimulating medical devices that form a part of the system can vary in form and function. Various representative embodiments of illustrative medical devices will be described.

A. Stimulation Probe

Figure 3A:
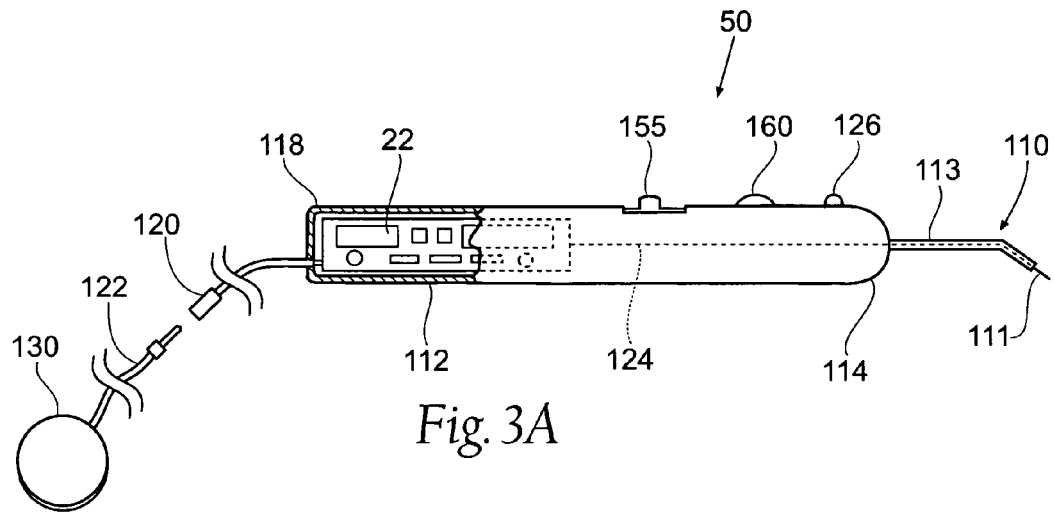
FIG. 3A is a side view with a portion broken away and in section showing the stimulation probe having the stimulation control device embedded within the stimulation probe.
Figure 3B:
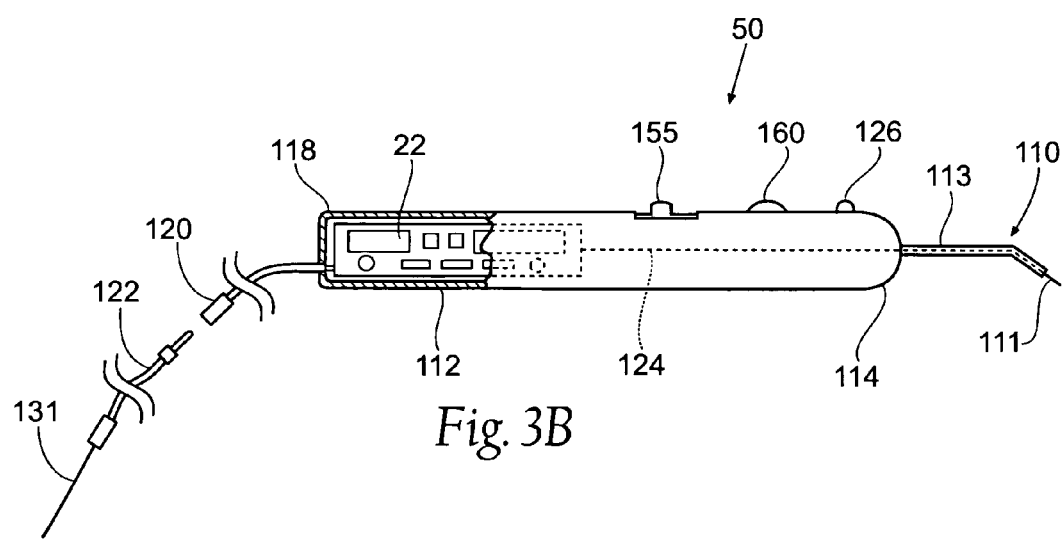
FIG. 3B is a side view with a portion broken away and in section showing the stimulation probe having the stimulation control device embedded within the stimulation probe, and showing an optional needle-like return electrode.
Figure 3C:
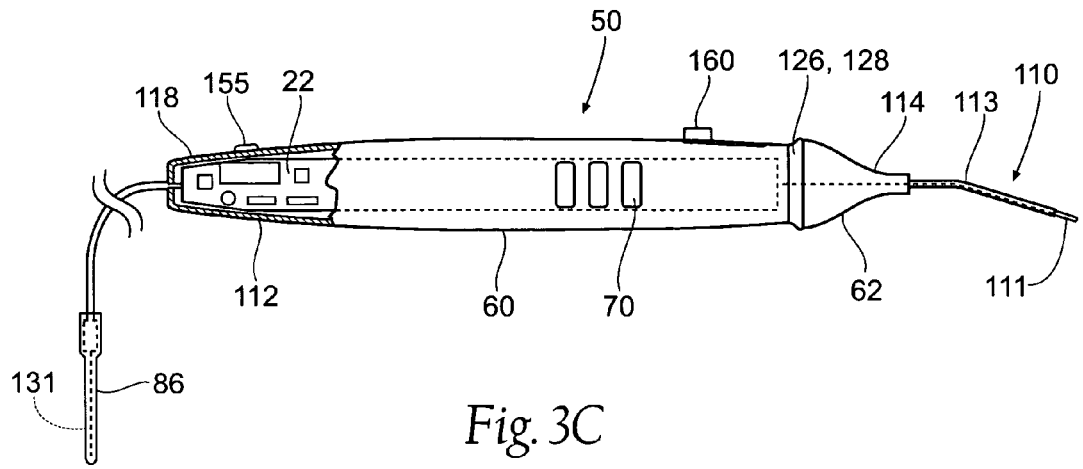
FIG. 3C is a side view with a portion broken away and in section showing an additional embodiment of the stimulation probe having a housing that includes a gripping base and a flexible nose cone, and an illuminating ring indicator.

FIGS. 3A to 3C show various embodiments of a hand held stimulation monitor or probe 50 for identification and testing of nerves and/or muscles during surgical procedures. As shown, the stimulation probe 50 may accommodate within a generally tubularly housing 112 the electrical circuitry of a stimulation control device 22. The stimulation probe 50 is desirably an ergonomic, sterile, single use instrument intended for use during surgical procedures to identify nerves and muscles, muscle attachments, or to contract muscles to assess the quality of surgical interventions or the need for surgical interventions, or to evaluate the function of nerves already identified through visual means. The stimulation probe 50 may be sterilized using ethylene oxide, for example.

The stimulation probe 50 is preferably sized small enough to be held and used by one hand during surgical procedures, and is ergonomically designed for use in either the left or right hand. In a representative embodiment, the stimulation probe 50 may have a width of about 20 millimeters to about 30 millimeters, and desirably about 25 millimeters. The length of the stimulation probe 50 (not including the operative element 110) may be about 18 centimeters to about 22 centimeters, and desirably about 20 centimeters. The operative element 110 may also include an angle or bend to facilitate access to deep as well as superficial structures without the need for a large incision. The operative element 110 will be described in greater detail later. A visual or audio indicator 126 incorporated with the housing 112 provides reliable feedback to the surgeon as to the request and delivery of stimulus current.

Figure 4A:
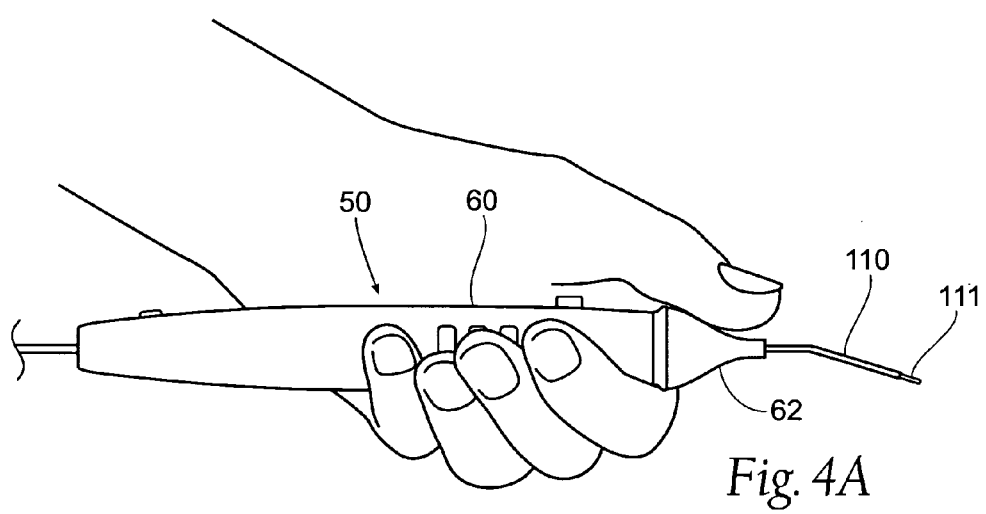
FIG. 4A is a side view of the stimulation probe of FIG. 3c, showing the users hand in a position on the stimulation probe to move the flexible nose cone.
Figure 4B:
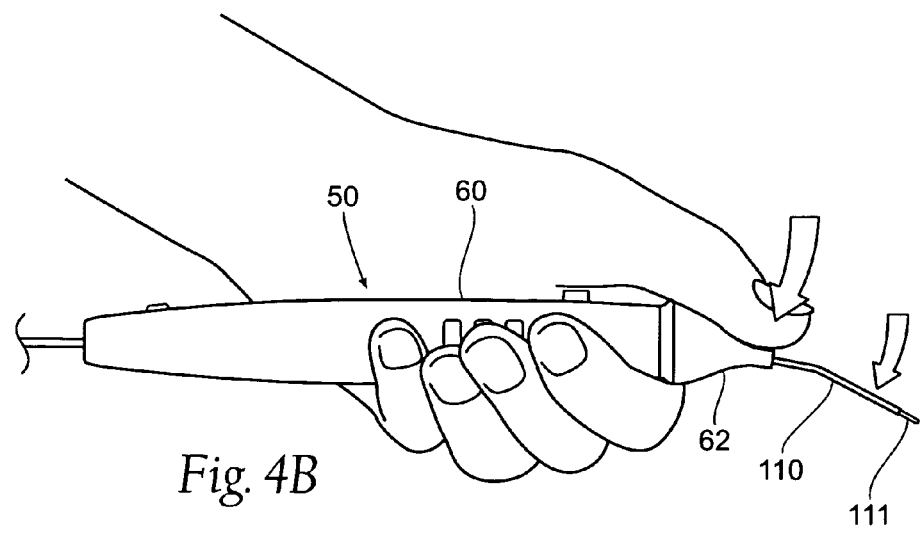
FIG. 4B is a side view of the stimulation probe of FIG. 4A, showing the users hand flexing the flexible nose cone.
Figure 14:
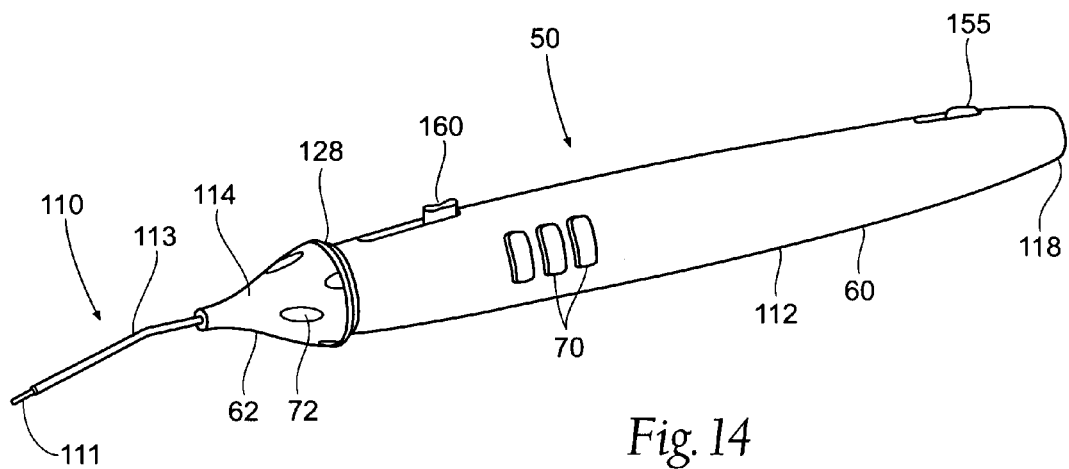
FIG. 14 is a perspective view of the stimulation probe shown in FIG. 3C.

In one embodiment shown in FIGS. 3C and 14, the stimulation probe 50 includes a housing 112 that comprises a gripping base portion 60 and an operative element adjustment portion 62. The operative element 110 extends from the proximal end of the adjustment portion 62. In order to aid the surgeon in the placement of the operative element 110 at the targeted tissue region, the adjustment portion, as will be described as a nose cone 62, may be flexible. This flexibility allows the surgeon to use either a finger or a thumb positioned on the nose cone 62 to make fine adjustments to the position of stimulating tip 111 of the operative element 110 at the targeted tissue region (see FIGS. 4A and 4B). The surgeon is able to grasp the gripping base 60 with the fingers and palm of the hand, and position the thumb on the nose cone 62, and with pressure applied with the thumb, cause the stimulating tip 111 to move while maintaining a steady position of the gripping base portion 62. This flexible nose cone 62 feature allows precise control of the position of the stimulating tip 111 with only the movement of the surgeon's thumb (or finger, depending on how the stimulating probe is held).

Figure 5:
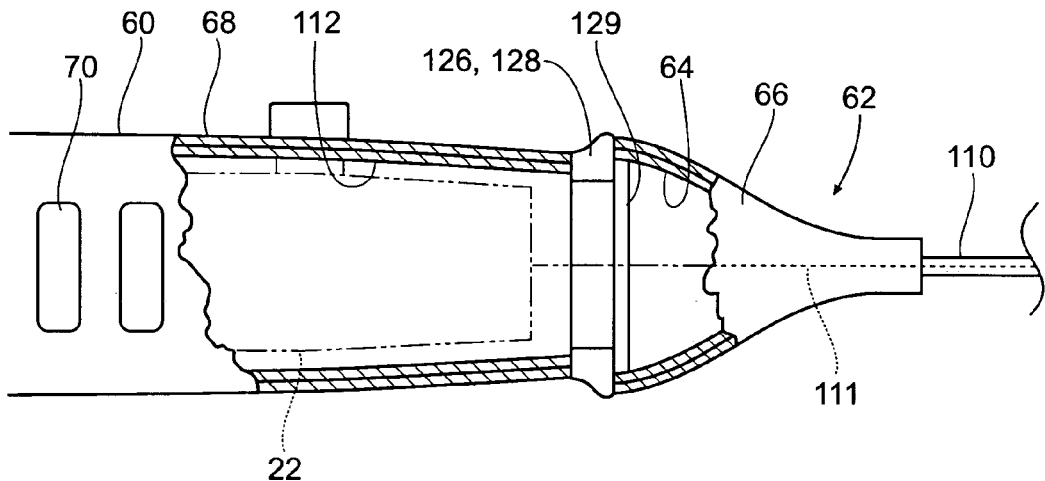
FIG. 5 is a side view with a portion broken away and in section showing elements of the flexible nose cone, the ring indicator, and the gripping base.

The flexible nose cone 62 may comprise a single element or it may comprise at least an inner portion 64 and an outer portion 66, as shown in FIG. 5. In order to facilitate some flexibility of the proximal portion 114 of the stimulation probe 50, the inner portion 64 of the nose cone 62 may be made of a thermoplastic material having some flexibility. One example may be LUSTRAN® ABS 348, or similar material. The outer portion 66 may comprise a softer over molded portion and may be made of a thermoplastic elastomer material having some flexibility. One example may be VERSAFLEX™ OM 3060-1 from GLS Corp. The nose cone 62 is desirably generally tapered. For example, the nose cone 62 may be rounded, as shown in FIGS. 3A and 3B, or the nose cone may be more conical in shape, as shown in FIG. 3C.

The nose cone 62 may also include one or more features, such as ribs or dimples 72, as shown in FIG. 14, to improve the gripping, control, and stability of the stimulation probe 50 within the surgeon's hand.

The gripping base portion 60 of the housing 112 may also include an overmolded portion 68. The overmolded portion 68 may comprise the full length of the gripping base portion 60, or only a portion of the gripping base 60. The soft overmolded portion 68 may include one or more features, such as dimples or ribs 70, as shown, to improve the gripping, control, and stability of the stimulation probe 50 within the surgeon's hand. The overmolded portion 68 may comprise the same or similar material as the thermoplastic elastomer material used for the outer portion 66 of the flexible nose cone 62.

In one embodiment, the stimulation probe 50 includes a housing 112 that carries an insulated lead 124. The insulated lead 124 connects the operative element 110 positioned at the housing's proximal end 114 to the circuitry 22 within the housing 112 (see FIG. 3A). It is to be appreciated that the insulated lead is not necessary and the operative element 110 may be coupled to the circuitry 22 (see FIG. 3C). The lead 124 within the housing 112 is insulated from the housing 112 using common insulating means (e.g., wire insulation, washers, gaskets, spacers, bushings, and the like). The conductive tip 111 of the operative element 110 is positioned in electrical conductive contact with at least one muscle, or at least one nerve, or at least one muscle and nerve.

As shown, the stimulation probe 50 is mono-polar and is equipped with a single operative element (i.e., electrode) 110 at the housing proximal end 114. A return electrode 130, 131 may be coupled to the stimulation probe 50 and may be any of a variety of electrode types (e.g., paddle, needle, wire, or surface), depending on the surgical procedure being performed. As shown, the various return electrodes 130, 131 are coupled to the housing distal end 118. In an alternative embodiment, the stimulation device 50 itself may be bipolar by including a return electrode in the operative element 110, which precludes the use of a return electrode coupled to the stimulation probe 50.

As shown and described, the stimulation probe 50 may accommodate within the housing 112 the electrical circuitry of a stimulation control device 22. In this arrangement, the stimulation probe 50 may have one or more user operable controls. Two are shown—155 and 160. Power switch 155 serves a dual purpose of turning the stimulation probe 500N and OFF (or standby), and also can be stepped to control the stimulation signal amplitude selection within a predefined range (e.g., 0.5, 2.0, and 20 mA). In this configuration, the switch may be a four position switch. Before the first use of the stimulation probe 50, the power switch 155 is in the OFF position and keeps the stimulation probe off. After the stimulation probe 50 has been turned ON—by moving the switch 155 to an amplitude selection—the OFF position now corresponds to a standby condition, where no stimulation would be delivered. In one embodiment, once the stimulation probe 50 has been turned on, it cannot be turned off, it can only be returned to the standby condition and will remain operational for a predetermined time, e.g., at least about seven hours. This feature is intended to allow the stimulation probe 50 to only be a single use device, so it can not be turned OFF and then used again at a later date.

The pulse control device 160 allows for adjustment of the stimulation signal pulse width from a predefined range (e.g., about zero to about 200 microseconds). In one embodiment, the pulse control 160 may be a potentiometer to allow a slide control to increase or decrease the stimulation signal pulse width within the predefined range.

The stimulation pulse may have a non-adjustable frequency in the range of about 10 Hz to about 20 Hz, and desirably about 16 Hz.

Figure 6:
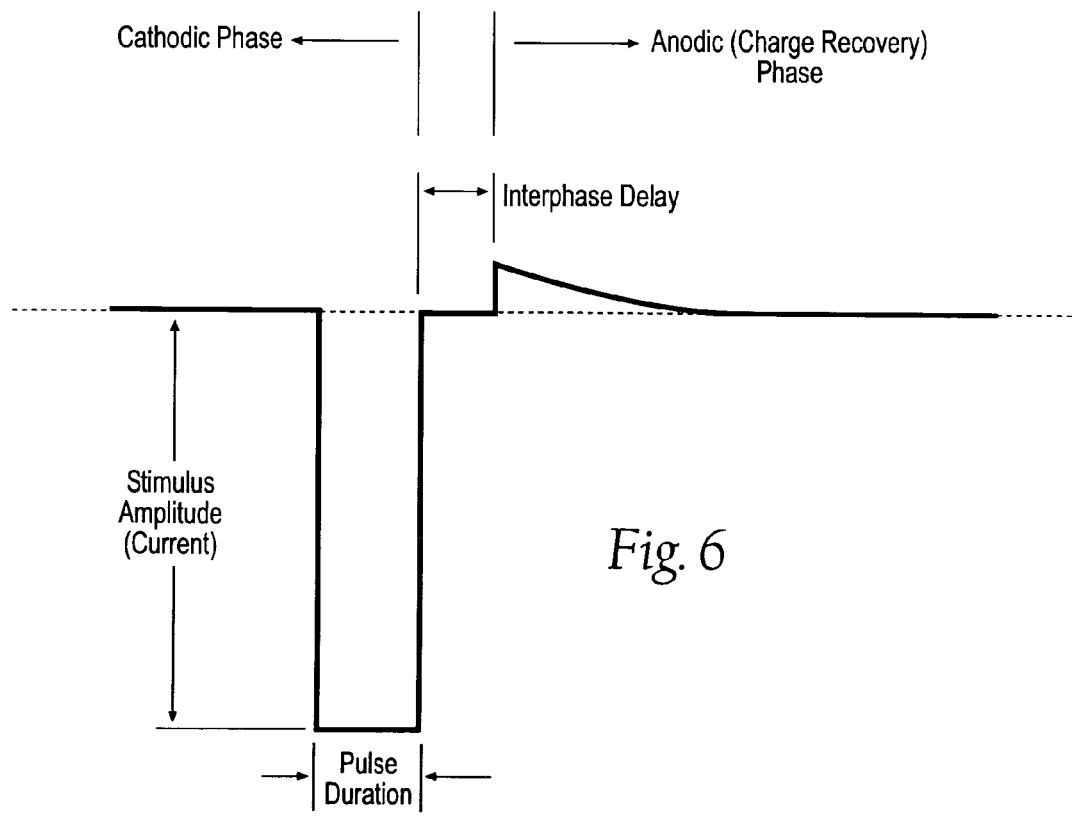
FIG. 6 is a graphical view of a desirable biphasic stimulus pulse output of the stimulation device.

As a representative example, the stimulation pulse desirably has a biphasic waveform with controlled current during the cathodic (leading) phase, and net DC current less than 10 microamps, switch adjustable from about 0.5 milliamps to about 20 milliamps, and pulse durations adjustable from about zero microseconds up to about 200 microseconds. A typical, biphasic stimulus pulse is shown in FIG. 6.

The operative element 110 exits the housing 112 at the proximal end 114 to deliver stimulus current to the excitable tissue. The operative element 110 comprises a length and a diameter of a conductive material, and is desirably fully insulated with the exception of the most proximal end, e.g. about 1.0 millimeters to about 10 millimeters, and desirably about 4 millimeters to about 6 millimeters, which is non-insulated and serves as the stimulating tip or surface (or also referred to as active electrode) 111 to allow the surgeon to deliver the stimulus current only to the intended tissue. The small area of the stimulating surface 111 (the active electrode) of the operative element 110 ensures a high current density that will stimulate nearby excitable tissue. The insulation material 113 may comprise a medical grade heat shrink.

The conductive material of the operative element 110 comprises a diameter having a range between about 0.5 millimeters to about 1.5 millimeters, and may be desirably about 1.0 millimeters. The length of the operative element 110 may be about 50 millimeters to about 60 millimeters, although it is to be appreciated that the length may vary depending on the particular application. As shown, the operative element 110 may include one or more bends to facilitate accurate placement of the stimulating surface 111. In one embodiment, the conductive material of operative element 110 is made of a stainless steel 304 solid wire, although other known conductive materials may be used.

As previously described, in monopolar operation, a return electrode (or indifferent electrode) 130 or 131, for example, provides an electrical path from the body back to the control device 22 within the housing 112. The return electrode 130 (see FIG. 3A) may be placed on the surface of intact skin (e.g., surface electrodes as used for ECG monitoring during surgical procedures) or it might be needle-like 131 (see FIGS. 3B and 3C), and be placed in the surgical field or penetrate through intact skin. The housing's distal end 118 can incorporate a connector or jack 120 which provides options for return current pathways, such as through a surface electrode 130 or a needle electrode 131, having an associated plug 122. It is to be appreciated that a return electrode and associated lead may be an integral part of the stimulation probe 50, i.e., no plug or connector, as shown in FIG. 3C.

Additionally, the device 50 may desirably incorporate a visual or audio indicator 126 for the surgeon. This visual or audio indicator 126 allows the surgeon to confirm that the stimulator 50 is delivering stimulus current to the tissue it is contacting. Through the use of different tones, colors, different flash rates, etc., the indicator 126 (which can take the form, e.g., of a light emitting diode (LED)) allows the surgeon to confirm that the stimulating tip 111 is in place, the instrument is turned ON, and that stimulus current is flowing. Thus the surgeon has a much greater confidence that the failure to elicit a muscle contraction is because of lack of viable nervous tissue near the tip 111 of the stimulator 50 rather than the failure of the return electrode connection or some other instrumentation problem.

As a representative example, in use the indicator 126 may be configured to illuminate continuously in one color when the stimulation probe 50 is turned on but not in contact with tissue. After contact with tissue is made, the indicator 126 may flash (i.e., blink) to indicate that stimulation is being delivered. If the stimulation has been requested, i.e., the stimulation probe has been turned on, but there is no stimulation being delivered because of a lack of continuity between the operative element 110 and the return electrode 130, or an inadequate connection of the operative element 110 or the return electrode 130 to the patient tissue, the indicator 126 may illuminate in a different color, and may illuminate continuously or may flash.

In one embodiment, as can be best seen in FIGS. 3C and 5, the indicator 126 comprises a ring indicator 128 that provides a visual indication around at least a portion, and desirably all of the circumference of the stimulation probe 50 generally near the flexible nose cone 62. The visual ring indicator 128 may be an element of the gripping portion 60, or it may be an element of the flexible nose cone 62, or the ring indicator may positioned between the gripping portion 60 and the flexible nose cone 62. The ring indicator 128 may also include a reflective element 129 to improve and focus the illumination effect of the light emitting source, e.g., one or more LEDs. The ring indicator 128 and the reflective element may be a single component, or more than one component (as can be seen in FIGS. 5 and 15).

Audio feedback also makes possible the feature of assisting the surgeon with monitoring nerve integrity during surgery. The insulated lead 124 connects to the operative element 110 that, in use, is positioned within the surgical field on a nerve distal to the surgical site. Stimulation of the nerve causes muscle contraction distally. The stimulation control device 22 incorporated within the housing 112 may be programmed to provide an audio tone followed by a stimulation pulse at prescribed intervals. The audio tone reminds the surgeon to observe the distal muscle contraction to confirm upon stimulation that the nerve is functioning and intact.

Figure 15:
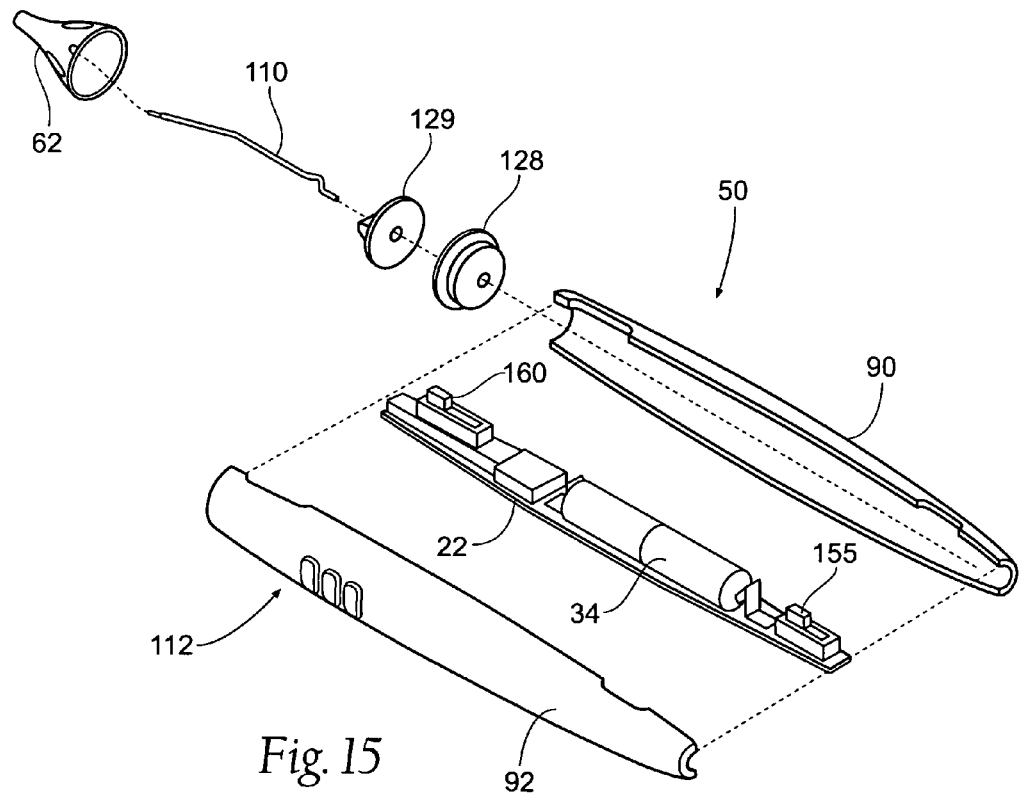
FIG. 15 is an exploded view of the stimulation probe shown in FIG. 14.

FIG. 15 shows an exploded view of a representative stimulation probe 50. As can be seen, the stimulation control device 22 is positioned within the housing 112. A battery 34 is electrically coupled to the control device 22. A first housing element 90 and a second housing element 92 partially encapsulate the control device 22. The ring indicator 128 and the reflective element 129 are coupled to the proximal end of the housing 112. The operative element 110 extends through the nose cone 62 and couples to the control device 22. Desirably, the stimulation probe 50 will be constructed in a manner to conform to at least the IPX1 standard for water ingress.

Figure 7:
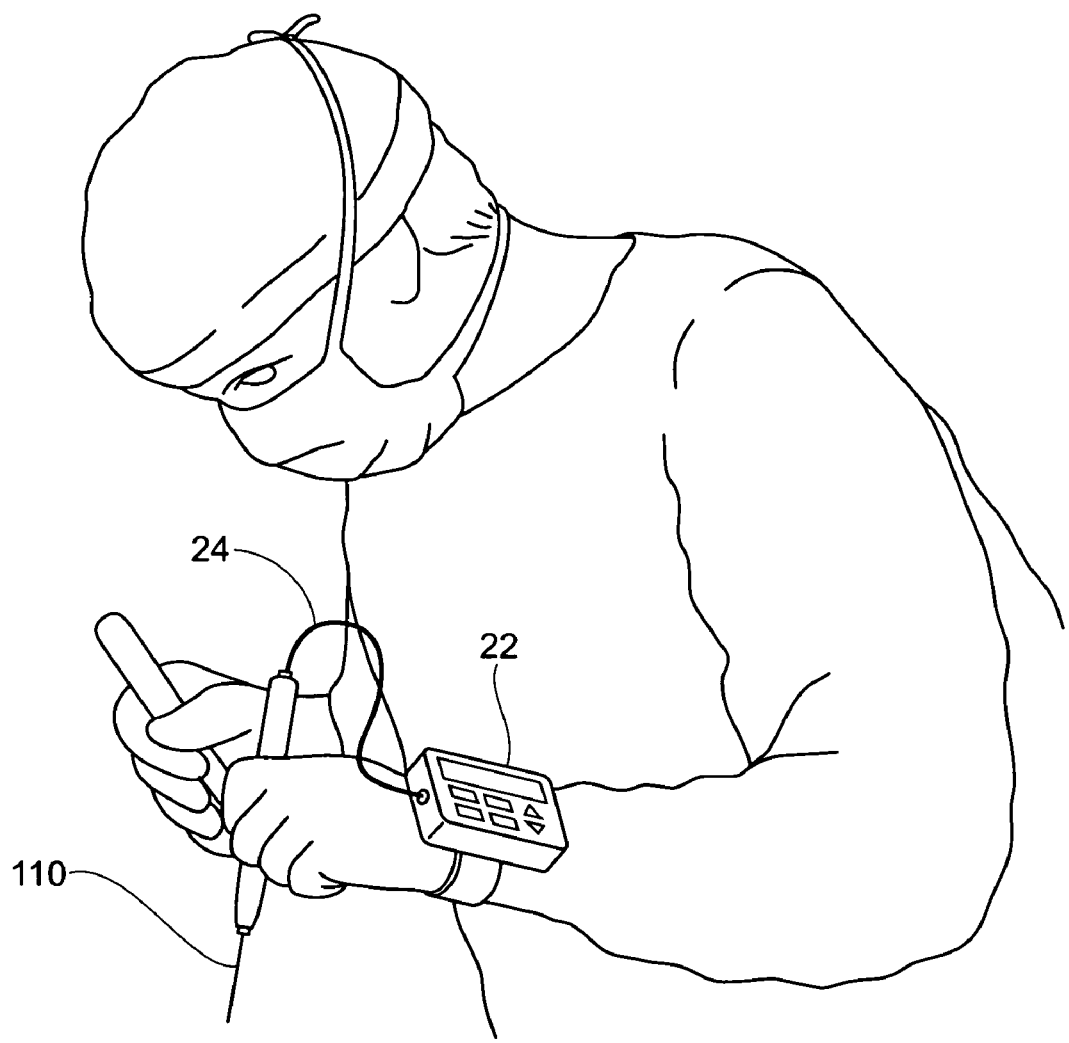
FIG. 7 is a view showing how the geometry of the stimulation control device shown in FIG. 2 aids in its positioning during a surgical procedure.

Alternatively, as FIG. 2 shows, the stimulation control device 22 may be housed in a separate case, with its own input/output (I/O) controls 26. In this alternative arrangement, the stimulation control device 22 is sized small enough to be easily removably fastened to a surgeon's arm or wrist during the surgical procedure, or otherwise positioned in close proximity to the surgical location (as shown in FIG. 7), to provide sufficient audio and/or visual feedback to the surgeon. In this arrangement, the separate stimulation control device 22 can be temporarily coupled by a lead to a family of various medical devices for use.

The present invention includes a method of identifying/locating tissue, e.g., a nerve or muscle, in a patient that comprises the steps of providing a hand-held stimulation probe 50, 100 as set forth above, engaging a patient with the first operative element 110 and the second electrode 130, moving the power switch 155 to an activation position causing a stimulation signal 29 to be generated by the stimulation control device 22 and transmitted to the first operative element 110, through the patient's body to the second electrode 130, and back to the stimulation control device 22. The method may also include the step of observing the indicator 126 to confirm the stimulation probe 50, 100 is generating a stimulation signal. The method may also include the step of observing a tissue region to observe tissue movement or a lack thereof.

B. The Stimulation Control Device

Figure 8:
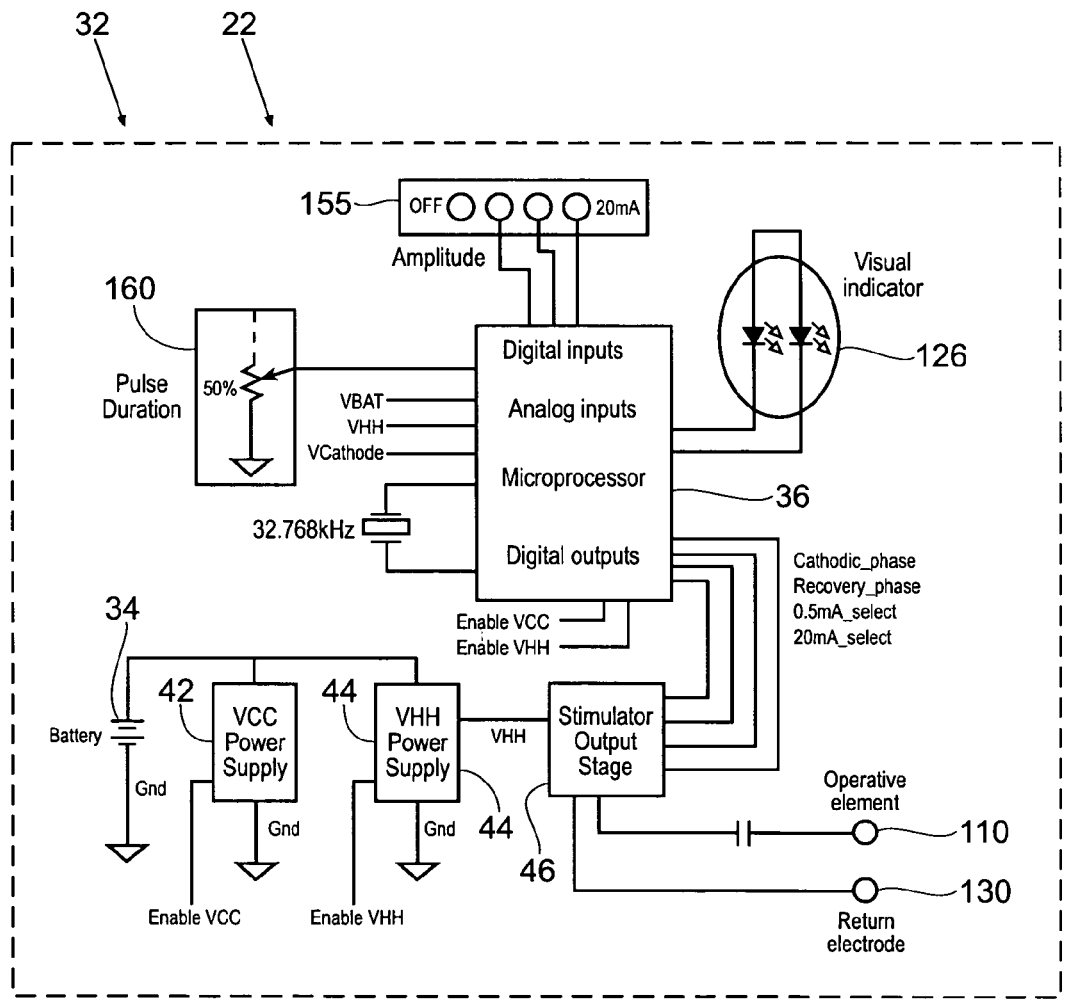
FIG. 8 is a block diagram of a circuit that the stimulation control device shown throughout the Figs. can incorporate.

As FIG. 8 shows, the stimulation control device 22 includes a circuit 32 that generates electrical stimulation waveforms. A battery 34 desirably provides the power. The control device 22 also desirably includes an on-board, programmable microprocessor 36, which carries embedded code. The code expresses pre-programmed rules or algorithms for generating the desired electrical stimulation waveforms using the stimulus output circuit 46 and for operating the visible or audible indicator 126 based on the controls actuated by the surgeon.

In one form, the size and configuration of the stimulation control device 22 makes for an inexpensive device, which is without manual internal circuit adjustments. It is likely that the stimulation control device 22 of this type will be fabricated using automated circuit board assembly equipment and methods.

C. Incorporation with Surgical Devices

A stimulation control device 22 as just described may be electrically coupled through a lead, or embedded within various devices commonly used in surgical procedures (as previously described for the stimulation probe 50).

1. Cutting Device

Figure 9A:
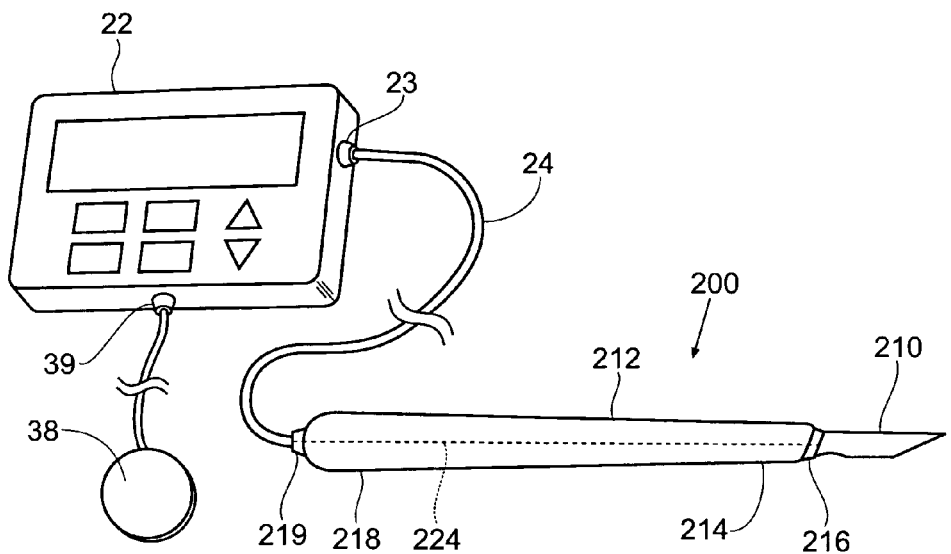
FIGS. 9A and 9B are perspective views showing the stimulation control device in use with a cutting device.
Figure 9B:
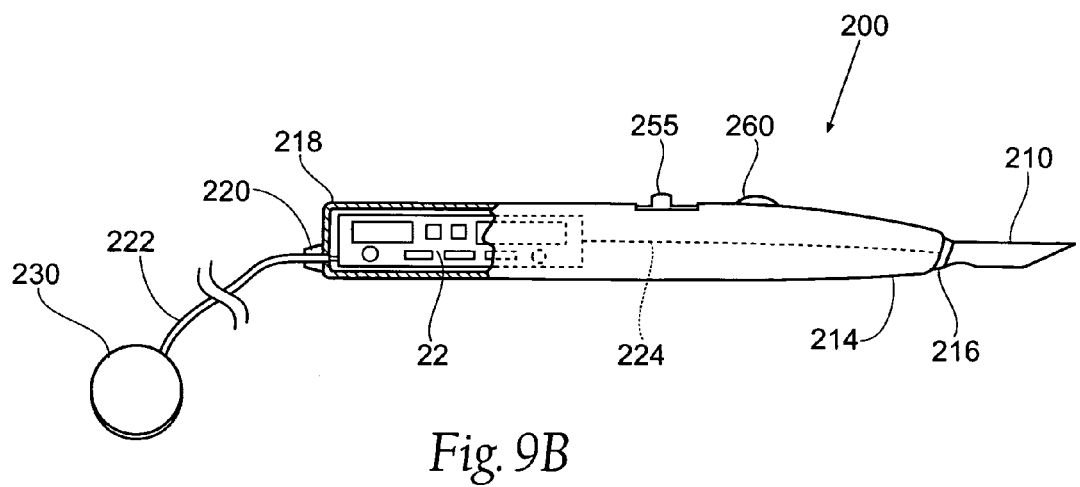

In FIGS. 9A and 9B, a device 200 is shown that incorporates all the features disclosed in the description of the stimulation probe 50, 100, except the device 200 comprises the additional feature of providing an "energized" surgical device or tool. FIG. 9A shows the tool to be a cutting device 200 (e.g., scalpel) removably coupled to a stimulation control device 22.

In the embodiment shown, the cutting device 200 includes a body 212 that carries an insulated lead 224. The insulated lead 224 connects to an operative element, such as electrode 210, positioned at the body proximal end 214 and a plug-in receptacle 219 at the body distal end 118. The lead 224 within the body 212 is insulated from the body 212 using common insulating means (e.g., wire insulation, washers, gaskets, spacers, bushings, and the like).

In this embodiment, the electrode 210 performs the cutting feature (e.g., knife or razor). The electrode 210 performs the cutting feature in electrical conductive contact with at least one muscle, or at least one nerve, or at least one muscle and nerve. The cutting device 200 desirably includes a plug-in receptacle 216 for the electrode 210, allowing for use of a variety of cutting electrode shapes and types (e.g., knife, razor, pointed, blunt, curved), depending on the specific surgical procedure being performed. In this configuration, the lead 224 electrically connects the electrode 210 to the stimulation control device 22 through plug-in receptacle 219 and lead 24.

In one embodiment, the cutting device 200 is mono-polar and is equipped with a single electrode 210 at the body proximal end 214. In the mono-polar mode, the stimulation control device 22 includes a return electrode 38 which functions as a return path for the stimulation signal. Electrode 38 may be any of a variety of electrode types (e.g., paddle, needle, wire, or surface), depending on the surgical procedure being performed. The return electrode 38 may be attached to the stimulation device 22 by way of a connector or plug-in receptacle 39. In an alternative embodiment, the cutting device 200 may be bipolar, which precludes the use of the return electrode 38.

In the embodiment shown in FIG. 9B, the cutting device 200 accommodates within the body 212 the electrical circuitry of the stimulation control device 22. In this arrangement, the cutting device 200 may have at least two operational slide controls, 255 and 260. Power switch 255 serves a dual purpose of turning the stimulation signal to the cutting device 200 on and off, and also is stepped to control the stimulation signal amplitude selection from a predefined range (e.g., 0.5, 2.0, and 20 mA). The pulse control switch 260 allows for adjustment of the stimulation signal pulse width from a predefined range (e.g., zero through 200 microseconds).

At the body distal end 218, a second plug-in receptacle 220 may be positioned for receipt of a second lead 222. Lead 222 connects to electrode 230 which functions as a return path for the stimulation signal when the cutting device 200 is operated in a mono-polar mode.

Additionally, the device 200 may incorporate a visual or audio indicator for the surgeon, as previously described.

The present invention includes a method of identifying/locating tissue, e.g., a nerve or muscle, in a patient that comprises the steps of providing cutting device 200 as set forth above, engaging a patient with the first electrode 210 and the second electrode 230, moving the power switch 255 to an activation position causing a stimulation signal 29 to be generated by the stimulation control device 22 and transmitted to the first electrode 210, through the patient's body to the second electrode 230, and back to the stimulation control device 22. The method may also include the step of observing the indicator 126 to confirm the cutting device 200 is generating a stimulation signal. The method may also include the step of observing a tissue region to observe tissue movement or a lack thereof.

2. Drilling Device

Figure 10A:
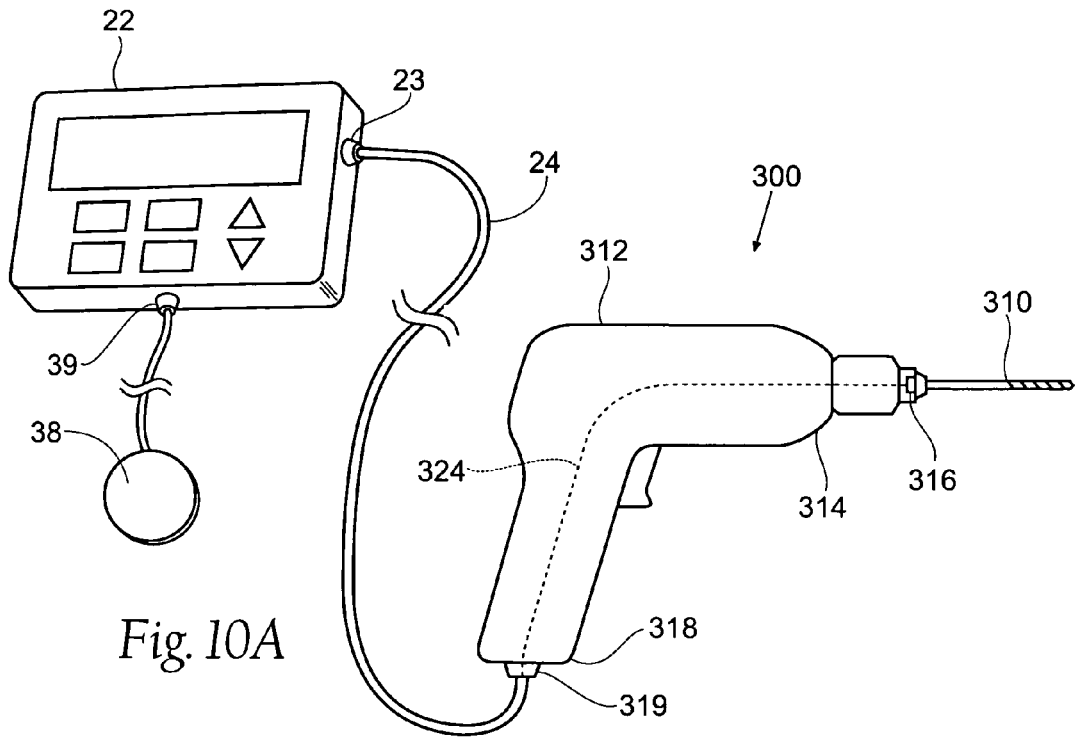
FIGS. 10A and 10B are perspective views showing the stimulation control device in use with a drilling or screwing device.
Figure 10B:
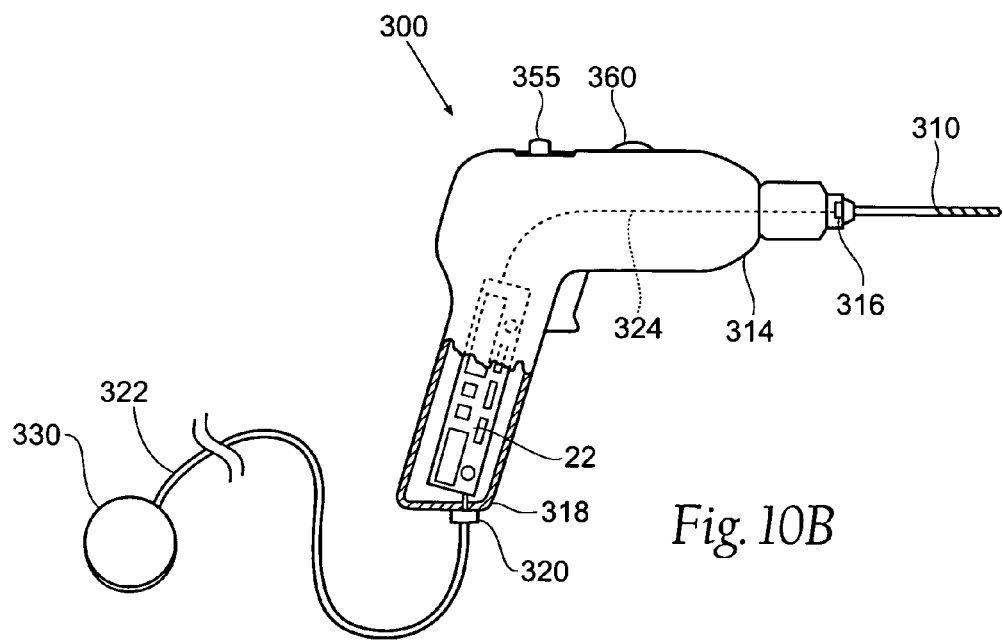

In FIGS. 10A and 10B, a device 300 is shown that incorporates all the features disclosed in the description of the stimulation probe 50, 100, except the device 300 comprises the additional feature of providing an "energized" surgical device or tool, which comprises a drilling device 300. In FIG. 10A is drilling device 300 is removably coupled to a stimulation control device 22.

In the embodiment shown, the drilling device 300 includes a body 312 that carries an insulated lead 324. The insulated lead 324 connects to an operative element, such as electrode 310, positioned at the body proximal end 314 and a plug-in receptacle 319 at the body distal end 318. The lead 324 within the body 312 is insulated from the body 312 using common insulating means (e.g., wire insulation, washers, gaskets, spacers, bushings, and the like).

In this embodiment, the electrode 310 performs the drilling feature. The electrode 310 may also perform a screwing feature as well. The electrode 310 performs the drilling feature in electrical conductive contact with a hard structure (e.g., bone).

The drilling device 300 desirably includes a plug-in receptacle or chuck 316 for the electrode 310, allowing for use of a variety of drilling and screwing electrode shapes and sizes (e.g., ¼ and ⅜ inch drill bits, Phillips and flat slot screw drivers), depending on the specific surgical procedure being performed. In this configuration, the lead 324 electrically connects the electrode 310 to the stimulation control device 22 through plug-in receptacle 319 and lead 324.

In one embodiment, the drilling device 300 is mono-polar and is equipped with a single electrode 310 at the body proximal end 314. In the mono-polar mode, the stimulation control device 22 includes a return electrode 38 which functions as a return path for the stimulation signal. Electrode 38 may be any of a variety of electrode types (e.g., paddle, needle, wire, or surface), depending on the surgical procedure being performed. The return electrode 38 may be attached to the stimulation device 22 by way of a connector or plug-in receptacle 39. In an alternative embodiment, the drilling device 300 may be bipolar, which precludes the use of the return electrode 38.

In FIG. 10B, the drilling device 300 is shown to accommodate within the body 312 the electrical circuitry of the stimulation control device 22. The drilling device 300 may have at least two operational slide controls, 355 and 360. Power switch 355 serves a dual purpose of turning the stimulation signal to the drilling device 300 on and off, and also is also stepped to control the stimulation signal amplitude selection from a predefined range (e.g., 0.5, 2.0, and 20 mA). The pulse control switch 360 allows for adjustment of the stimulation signal pulse width from a predefined range (e.g., zero through 200 microseconds). At the body distal end 318, a second plug-in receptacle 320 may be positioned for receipt of a second lead 322. Lead 322 connects to electrode 330 which functions as a return path for the stimulation signal when the drilling device 300 is operated in a mono-polar mode.

Additionally, the device 300 may incorporate a visual or audio indicator for the surgeon, as previously described.

The present invention includes a method of identifying/locating tissue, e.g., a nerve or muscle, in a patient that comprises the steps of providing a drilling device 300 as set forth above, engaging a patient with the first electrode 310 and the second electrode 330, moving the power switch 355 to an activation position causing a stimulation signal 29 to be generated by the stimulation control device 22 and transmitted to the first electrode 310, through the patient's body to the second electrode 330, and back to the stimulation control device 22. The method may also include the step of observing the indicator 126 to confirm the drilling device 400 is generating a stimulation signal. The method may also include the step of observing a tissue region to observe tissue movement or a lack thereof.

3. Pilot Auger

An additional aspect of the invention provides systems and methods for controlling operation of a family of stimulating devices comprising a stimulation control device electrically coupled to a pilot auger for hard surface rotary probing.

Figure 11A:
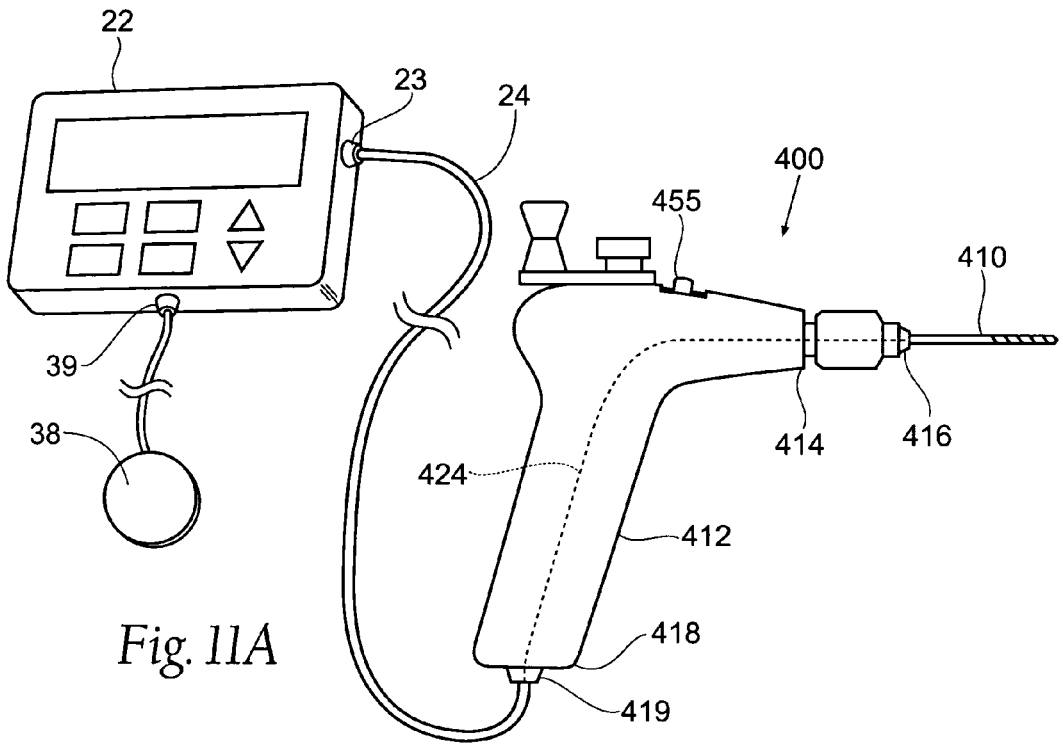
FIGS. 11A and 11B are perspective views showing the stimulation control device in use with a pilot auger device.

This embodiment incorporates all the features disclosed in the description of the stimulation probe 50, 100, except this embodiment comprises the additional feature of providing an "energized" surgical device or tool. FIG. 11A shows a pilot auger device 400 removably coupled to a stimulation control device 22. In the embodiment shown, the pilot auger device 400 includes a body 412 that carries an insulated lead 424. The insulated lead 424 connects to an operative element, such as an electrode 410, positioned at the body proximal end 414 and a plug-in receptacle 419 at the body distal end 418. The lead 424 within the body 412 is insulated from the body 412 using common insulating means (e.g., wire insulation, washers, gaskets, spacers, bushings, and the like). In this embodiment, the electrode 410 performs the pilot augering feature. The electrode 410 performs the pilot augering feature in electrical conductive contact with a hard structure (e.g., bone).

The pilot auger device 400 desirably includes a plug-in receptacle or chuck 416 for the electrode 410, allowing for use of a variety of pilot augering electrode shapes and sizes (e.g., 1/32, 1/16, and 1/8 inch), depending on the specific surgical procedure being performed. In this configuration, the lead 24 electrically connects the electrode 410 to the stimulation control device 22 through plug-in receptacle 419 and lead 24.

In one embodiment, the pilot auger device 400 is monopolar and is equipped with a single electrode 410 at the body proximal end 414. In the mono-polar mode, the stimulation control device 22 includes a return electrode 38 which functions as a return path for the stimulation signal. Electrode 38 may be any of a variety of electrode types (e.g., paddle, needle, wire, or surface), depending on the surgical procedure being performed. The return electrode 38 may be attached to the stimulation device 22 by way of a connector or plug-in receptacle 39. In an alternative embodiment, the pilot auger device 400 may be bipolar, which precludes the use of the return electrode 38.

Figure 11B:
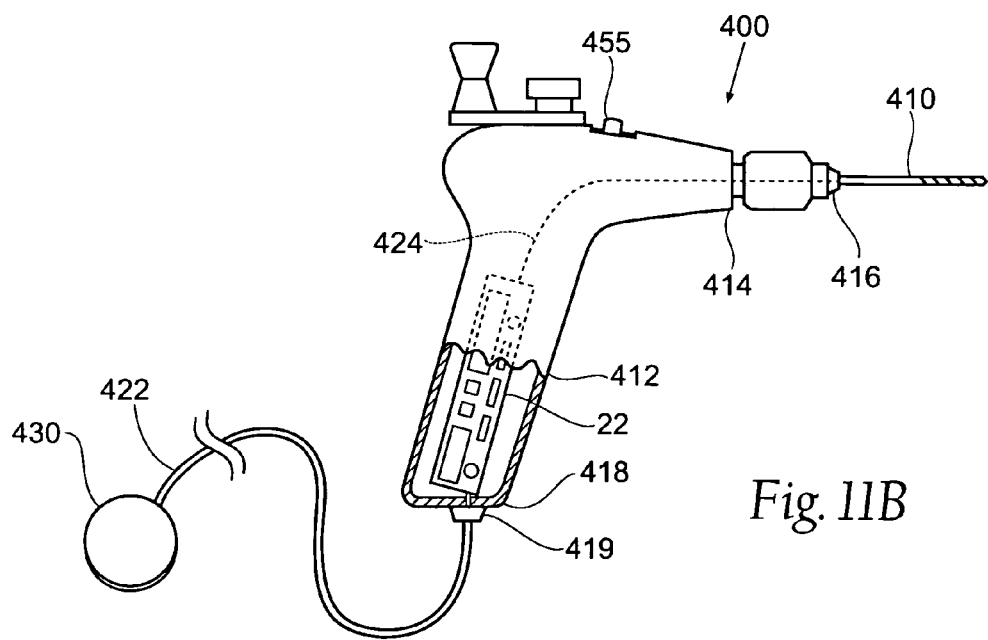

As FIG. 11B shows, the pilot auger device 400 may accommodate within the body 412 the electrical circuitry of the stimulation control device 22. At the body distal end 418, a second plug-in receptacle 420 may be positioned for receipt of a second lead 422. Lead 422 connects to electrode 430 which functions as a return path for the stimulation signal when the pilot auger device 400 is operated in a mono-polar mode.

The pilot auger device 400 includes a power switch 455. When moved to an activation position, a stimulation signal is generated by the stimulation control device 22. Additionally, the device 400 may incorporate a visual or audio indicator for the surgeon, as previously described.

The present invention includes a method of identifying/locating tissue, e.g., a nerve or muscle, in a patient that comprises the steps of providing a pilot auger device 400 as set forth above, engaging a patient with the first electrode 410 and the second electrode 430, moving the power switch 455 to an activation position causing a stimulation signal to be generated by the stimulation control device 22 and transmitted to the first electrode 410, through the patient's body to the second electrode 430, and back to the stimulation control device 22. The method may also include the step of observing the indicator 126 to confirm the pilot auger device 400 is generating a stimulation signal. The method may also include the step of observing a tissue region to observe tissue movement or a lack thereof.

D. Incorporation with Fixation Devices

An additional aspect of the invention provides systems and methods for controlling operation of a family of stimulating devices comprising a stimulation control device electrically coupled to a fixation device or a wrench or screwdriver for placing the fixation device. A fixation device (e.g., orthopedic hardware, pedicle screws) is commonly used during spinal stabilization procedures (fusion), and internal bone fixation procedures.

Figure 12A:
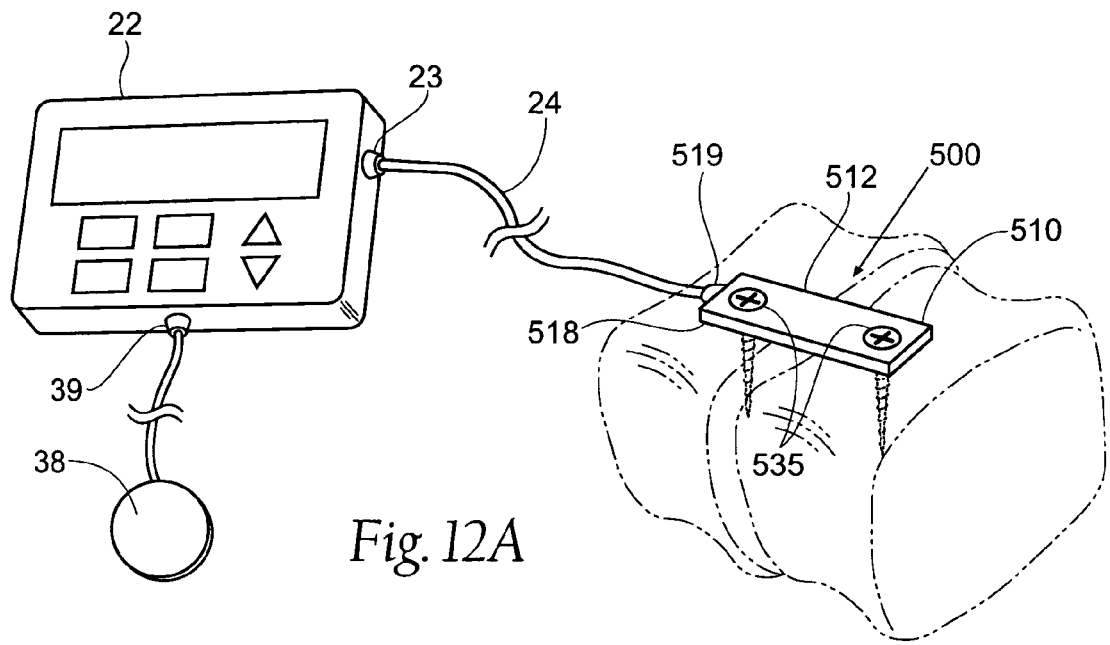
FIGS. 12A and 12B are perspective views showing the stimulation control device in use with a fixation device.

This embodiment incorporates all the features disclosed in the description of the stimulation probe 50, 100, except this embodiment comprises the additional feature of providing an "energized" fixation device or tool. FIG. 12A shows a fixation device 500 removably coupled to a stimulation control device 22. In the embodiment shown, the fixation device 500 includes a rectangularly shaped body 512 that also serves as an operative element, such as electrode 510. The fixation device 500 may take on an unlimited number of shapes as necessary for the particular procedure taking place. Pedicle screws 535 may be used to secure the fixation device to the bony structure. The electrode 510 performs the fixation feature in electrical conductive contact with a hard structure (e.g., bone).

The fixation device 500 or wrench or screwdriver for placing the fixation device desirably includes a plug-in receptacle 519. The fixation device 500 may take on an unlimited variety of shapes and sizes depending on the specific surgical procedure being performed. In this configuration, the lead 24 electrically connects the electrode 510 to the stimulation control device 22 through plug-in receptacle 519.

In one embodiment, the fixation device 500 is mono-polar and is equipped with the single electrode 510. In the mono-polar mode, the stimulation control device 22 includes a return electrode 38 which functions as a return path for the stimulation signal. Electrode 38 may be any of a variety of electrode types (e.g., paddle, needle, wire, or surface), depending on the surgical procedure being performed. The return electrode 38 may be attached to the stimulation device 22 by way of a connector or plug-in receptacle 39. In an alternative embodiment, the fixation device 500 may be bipolar, which precludes the use of the return electrode 38.

Figure 12B:
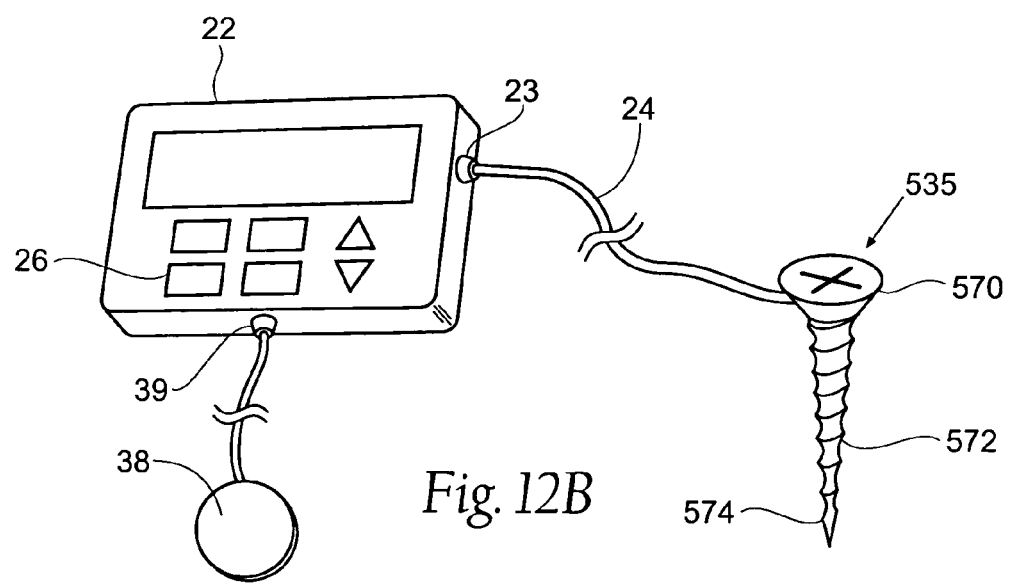
Figure 13:
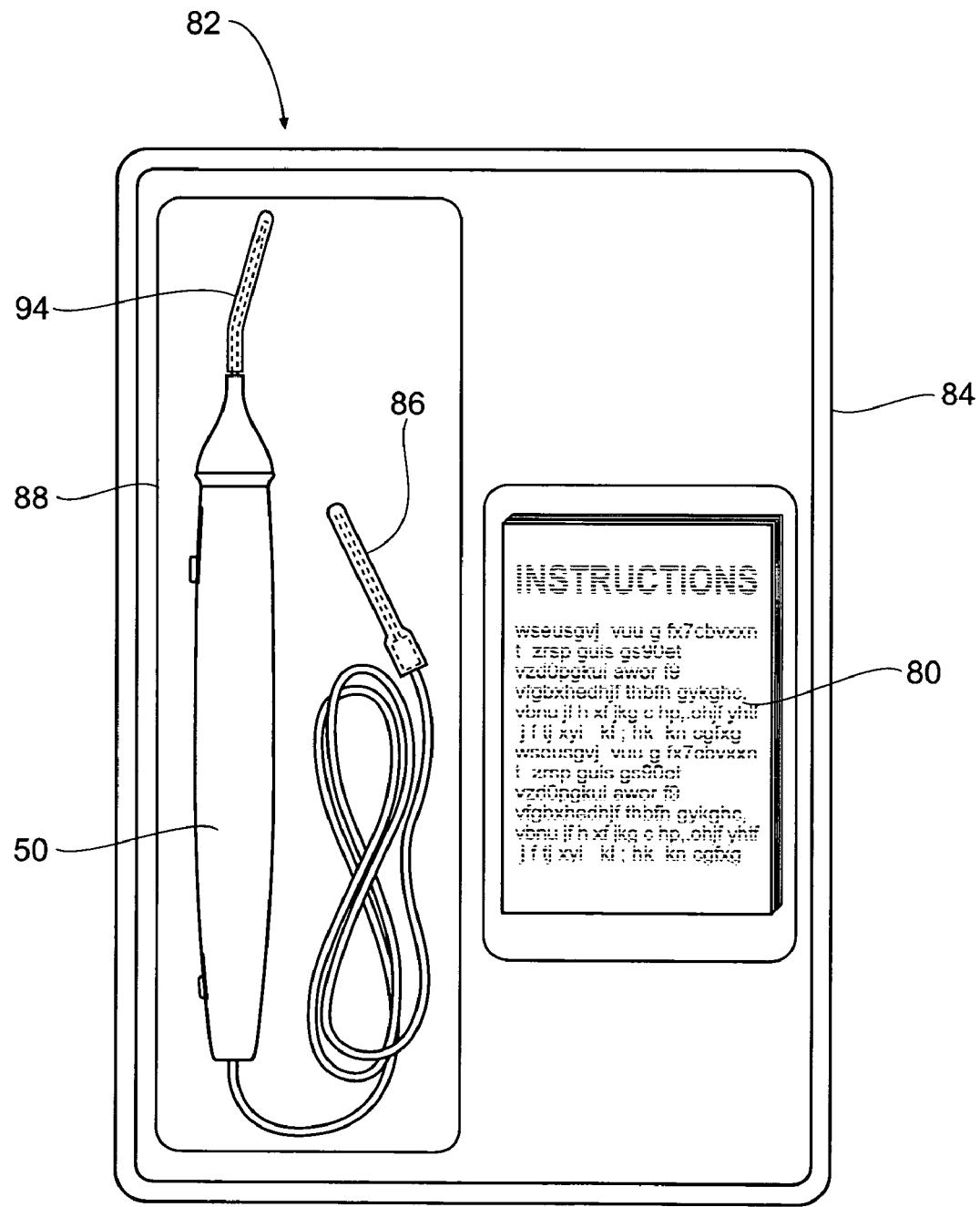
FIG. 13 is a plane view of a kit used in conjunction with the stimulation probe shown in FIG. 3C, and including the stimulation probe and instructions for use.

In yet an additional alternative embodiment (see FIG. 12B), the fixation device may be a pedicle screw 535. The pedicle screw 535 is removably coupled to a stimulation control device 22. In the embodiment shown, the pedicle screw 535 includes a head 570 and a shaft 572, which both serve as an operative element, such as electrode 574. The electrode 574 performs the fixation feature in electrical conductive contact with a hard structure (e.g., bone), as the pedicle screw 535 is being positioned within a bony structure. The lead 24 electrically connects the electrode 574 to the stimulation control device 22, through a break-away connection or other similar electrical connective means. The fixation device 535 may take on an unlimited variety of shapes and sizes depending on the specific surgical procedure being performed.

In the mono-polar mode, the stimulation control device 22 includes a return electrode 38 which functions as a return path for the stimulation signal. Electrode 38 may be any of a variety of electrode types (e.g., paddle, needle, wire, or surface), depending on the surgical procedure being performed. In an alternative embodiment, the fixation device 500 may be bipolar, which precludes the use of the return electrode 38.

The present invention includes a method of identifying/locating tissue, e.g., a nerve or muscle, in a patient that comprises the steps of providing a fixation device 500 as set forth above, engaging a patient with the first electrode 510 and the second electrode 38, turning power on to the stimulation control device 22 through the I/O controls 26, causing a stimulation signal 29 to be generated by the stimulation control device 22 and transmitted to the first electrode 510, through the patient's body to the second electrode 38, and back to the stimulation control device 22. The method may also include the step of observing the indicator 126 to confirm the fixation device 500 is generating a stimulation signal. The method may also include the step of observing a tissue region to observe tissue movement or a lack thereof.

IV. Technical Features

The stimulation control device 22, either alone or when incorporated into a stimulation probe or surgical device, can incorporate various technical features to enhance its universality.

A. Small Size

According to one desirable technical feature, the stimulation control device 22 can be sized small enough to be held and used by one hand during surgical procedures, or to be installed within a stimulation probe or surgical device. The angle of the stimulating tip facilitates access to deep as well as superficial structures without the need for a large incision. Visual and/or audible indication incorporated in the housing provides reliable feedback or status to the surgeon as to the request and delivery of stimulus current.

According to an alternative desirable technical feature, the stimulation control device 22 may also be sized small enough to be easily removably fastened to a surgeon's arm or wrist during the surgical procedure, or positioned in close proximity to the surgical location (as shown in FIG. 7), to provide sufficient audio and/or visual feedback to the surgeon.

B. Power Source

According to one desirable technical feature, power is provided by one or more primary batteries 34 for single use positioned inside the housing and coupled to the control device 22. A representative battery 34 may include a size "N" alkaline battery. In one embodiment, two size "N" alkaline batteries in series are included to provide a 3 volt power source. This configuration is sized and configured to provide an operating life of at least seven hours of operation—either continuous or intermittent stimulation.

C. The Microprocessor/Microcontroller

According to one desirable technical feature, the stimulation control device 22 desirably uses a standard, commercially available micro-power, flash programmable microcontroller 36. The microcontroller 36 reads the controls operated by the surgeon, controls the timing of the stimulus pulses, and controls the feedback to the user about the status of the instrument (e.g., an LED with 1, 2, or more colors that can be on, off, or flashing).

The microcontroller operates at a low voltage and low power. The microcontroller send low voltage pulses to the stimulus output stage 46 that converts these low voltage signals into the higher voltage, controlled voltage, or controlled current, stimulus pulses that are applied to the electrode circuit. This stimulus output stage 46 usually involves the use of a series capacitor to prevent the presence of DC current flow in the electrode circuit in normal operation or in the event of an electronic component failure.

V. Representative Use of a Stimulation Probe

The stimulation probe 50, 100, as described, make possible the application of a stimulation signal at sufficiently high levels for the purposes of locating, stimulating, and evaluating nerve or muscle, or both nerve and muscle integrity in numerous medical procedures, including, but not limited to, evaluating proximity to a targeted tissue region, evaluating proximity to a nerve or to identify nerve tissue, evaluating if a nerve is intact (i.e., following a traumatic injury) to determine if a repair may be needed, evaluating muscle contraction to determine whether or not the muscle is innervated and/or whether the muscle is intact and/or whether the muscle is severed, and evaluating muscle and tendon length and function following a repair or tendon transfer prior to completing a surgical procedure.

Instructions for use 80 are desirably included in a kit 82 along with a stimulation probe 50. The kit 82 can take various forms. In the illustrated embodiment, kit 82 comprises a sterile, wrapped assembly. A representative kit 82 includes an interior tray 84 made, e.g., from die cut cardboard, plastic sheet, or thermo-formed plastic material, which hold the contents. Kit 82 also desirably includes instructions for use 80 for using the contents of the kit to carry out a desired therapeutic and/or diagnostic objectives.

The instructions 80 guide the user through the steps of unpacking the stimulation probe 50, positioning the electrodes, and disposing of the single use disposable stimulator 50. Representative instructions may include, but are not limited to:

Remove the stimulation probe 50 from sterile package 88.
Remove cover 94 (e.g., a silicone cover) from the operative element 110.
Remove protective cover 86 from the return electrode 131.
Position the return electrode 131 in contact with the patient such that:
1. The return electrode is desirably positioned in an area remote from the area to be stimulated.
2. The return electrode is desirably not positioned across the body from the side being stimulated.
3. The return electrode is desirably not in muscle tissue.
Turn the stimulation probe 50 ON by moving the power switch 155 from OFF to the 0.5 mA setting (or greater). The stimulation probe 50 desirably is turned ON before the operative element 110 makes contact with tissue.
The indicator 126 will be illuminated yellow (for example) continuously if the stimulation probe 50 is ON, but not in contact with tissue.
Contact tissue with the operative element 110.
Adjust the pulse control 160 gradually to increase the level of stimulation. The indicator 126 will flash yellow indicating that stimulation is being delivered.
A flashing red (for example) indicator 126 means that stimulation has been requested, but no stimulation is being delivered because of inadequate connection of the operative element 110 or the return electrode 131 to the patient tissue. Check the return electrode contact and position, and check the operative element 110 contact and position.

Placing the power switch 155 to the off/standby position will stop stimulation and the visual indictor 126 will be illuminated yellow continuously.

Placing the pulse control 160 at the minimum position will stop stimulation and the visual indictor 126 will be illuminated yellow continuously.

A low/depleted battery 34 will cause the stimulation probe 50 to automatically turn OFF and the visual indicator 126 will not be illuminated. No further use of the stimulator 50 will be possible.

At end of use, move the power switch 155 to the off/standby position and move the pulse control 160 to the minimum position.

Cut off and dispose of the return electrode 131 in an appropriate sharps/biohazard container.

Dispose of the stimulation probe 50 per hospital or facility guidelines.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A hand-held tissue stimulation system comprising:
    a tubular housing having a proximal end and a distal end, the housing being sized and configured to be held and controlled entirely within a surgical field and in a single hand by a user, the housing including a flexible probe adjustment portion including an elastic material extending from the distal end,
    a stimulation control device positioned entirely within the housing, the stimulation control device comprising stimulation signal generating circuitry for generation of an electrical stimulation signal having an amplitude and a duration, a microcontroller electrically coupled to the stimulation signal generating circuitry, and a source of power for the stimulation control device,
    a probe extending from the flexible probe adjustment of the housing and having an electrically conductive surface coupled to the signal generating circuitry, the electrically conductive surface being sized and configured for contact with a targeted tissue region and, when in contact, applying the electrical stimulation signal to the targeted tissue region, the flexible probe adjustment portion being sized and configured to elastically flex in response to pressure applied by a finger or a thumb of the hand holding the housing to adjust position of the electrically conductive surface at the targeted tissue region,
    a return electrode electrically coupled to the signal generating circuitry and being sized and configured for contact with tissue to provide an electrical flow path for the stimulation signal from the probe back to the stimulation control device,
    a first control device carried on the housing and electrically coupled to the microcontroller, the first control device being movable by a user from a first position to a second position for providing a power control input to the microcontroller to turn the stimulation signal generating circuitry on only for a predetermined total single use period, the first control device also being movable from the second position back to the first position for providing a control input to the microcontroller to place the stimulation signal generating circuitry in a power-on, standby condition during the predetermined total single use period, the first control device also being movable from the second position through a plurality of control positions for providing amplitude control inputs to the microcontroller to control selection of the amplitude within a predefined amplitude range during the total single use period,
    a second control device carried on the housing separate from the first control device and being electrically coupled to the microcontroller, the second control device comprising a potentiometer operable by a user during the total single use period independent of the first control device within a range of control positions for providing duration control inputs to the microcontroller to control adjustment of the duration from a predefined duration range, and
    a single visual indicator carried on the housing and being electrically coupled to the microcontroller for confirming status conditions during the total single use period including visual indications that vary according to different status conditions, the microcontroller configured to cause the single visual indicator to display: (i) a first predetermined color and/or flash rate of light confirming, independent of contact between the probe and the targeted tissue region, that power to the stimulation signal generating circuitry is on due to operation of the first control device, (ii) a second predetermined color and/or flash rate of light different than the first predetermined color and/or flash rate of light confirming, when there is contact between the probe and the targeted tissue region, the delivery of the stimulation signal to the targeted tissue region through the probe and back to the stimulation control device through the return electrode due to operation of the first and/or second control device, and (iii) a third predetermined color and/or flash rate of light different than the first predetermined color and/or flash rate of light and the second predetermined color and/or flash rate of light indicating, when there is contact between the probe and the targeted tissue region, an absence of delivery of the stimulation signal back to the stimulation control device through the return electrode despite operation of the first and/or second control device.

2. A hand-held tissue stimulation system according to claim 1
    wherein the stimulation signal is adapted to provide a physical motor response.

3. A hand-held tissue stimulation system according to claim 1
    wherein the stimulation signal is adapted to provide an indication of an intact nerve to determine if a repair is needed.

4. A hand-held tissue stimulation system according to claim 1
    wherein the stimulation signal is adapted to provide, an indication of a muscle condition to identify whether the muscle is innervated or whether the muscle is intact or whether the muscle is severed.

5. A hand-held tissue stimulation system according to claim 1
    wherein the stimulation signal is adapted to provide an indication of muscle and tendon length and function following a repair or tendon transfer prior to completing a surgical procedure.

6. A hand-held tissue stimulation system according to claim 1 wherein the probe is non-linear in shape.

7. A hand-held tissue stimulation system according to claim 1
wherein the single visual indicator comprises a single illuminating circumferential ring indicator, sized and configured for visibility around an entire circumference of the housing.

8. A hand-held tissue stimulation system according to claim 7
wherein the single illuminating circumferential ring indicator further includes a reflector element.

9. A hand-held tissue stimulation system according to claim 1
wherein the predefined amplitude range includes about zero milliamps and increases to milliamp values greater than about zero.

10. A hand-held tissue stimulation system according to claim 9
wherein the predefined amplitude range includes about zero milliamps and increases in steps to about 20 milliamps.

11. A hand-held tissue stimulation system according to claim 1
wherein the predefined duration range includes about zero microseconds and increases through microsecond values greater than about zero.

12. A hand-held tissue stimulation system according to claim 11
wherein the predefined duration range includes about zero microseconds and increases through about 200 microseconds.

* * * * *

UNITED STATES PATENT AND TRADEMARK OFFICE
CERTIFICATE OF CORRECTION

| | |
|---|---|
| PATENT NO. | : 7,878,981 B2 |
| APPLICATION NO. | : 11/651165 |
| DATED | : February 1, 2011 |
| INVENTOR(S) | : Strother et al. |

It is certified that error appears in the above-identified patent and that said Letters Patent is hereby corrected as shown below:

Column 18, claim 4, line 58, after "provide" delete ",".

Column 19, claim 7, line 6, after "indicator" delete ",".

Signed and Sealed this
Twenty-eighth Day of June, 2011

David J. Kappos
*Director of the United States Patent and Trademark Office*